(12) United States Patent
Abunassar

(10) Patent No.: US 12,048,448 B2
(45) Date of Patent: Jul. 30, 2024

(54) LEAFLET GRASPING AND CUTTING DEVICE

(71) Applicant: Evalve, Inc., Santa Clara, CA (US)

(72) Inventor: Chad J. Abunassar, Alameda, CA (US)

(73) Assignee: Evalve, Inc., Santa Clara, CA (US)

( * ) Notice: Subject to any disclaimer, the term of this patent is extended or adjusted under 35 U.S.C. 154(b) by 407 days.

(21) Appl. No.: 17/306,412

(22) Filed: May 3, 2021

(65) Prior Publication Data
US 2021/0346045 A1 Nov. 11, 2021

Related U.S. Application Data

(60) Provisional application No. 63/020,662, filed on May 6, 2020.

(51) Int. Cl.
*A61B 17/295* (2006.01)
*A61B 17/00* (2006.01)
(Continued)

(52) U.S. Cl.
CPC .... *A61B 17/295* (2013.01); *A61B 17/320016* (2013.01); *A61B 17/3476* (2013.01);
(Continued)

(58) Field of Classification Search
CPC ........ A61B 17/295; A61B 2017/00243; A61B 2017/00783; A61B 2017/2947;
(Continued)

(56) References Cited

U.S. PATENT DOCUMENTS

| 1,996,261 A | 4/1935 | Storz |
| 2,097,018 A | 10/1937 | Chamberlin |
| (Continued) | | |

FOREIGN PATENT DOCUMENTS

| CN | 1469724 A | 1/2004 |
| CN | 102770080 A | 11/2012 |
| (Continued) | | |

OTHER PUBLICATIONS

Nishimura, et al. 2014 AHA/ACC guideline for the management of patients with valvular heart disease: executive summary: a report of the American College of Cardiology/American Heart Association Task Force on Practice Guidelines. J Am Coll Cardiol. Jun. 10, 2014; 63(22):2438-88.
(Continued)

*Primary Examiner* — Katherine H Schwiker
*Assistant Examiner* — Zehra Jaffri
(74) *Attorney, Agent, or Firm* — Workman Nydegger

(57) ABSTRACT

A system configured to cut leaflet tissue at a cardiac valve may comprise a guide catheter and a cutting mechanism routable through the guide catheter. The cutting mechanism includes a cutting arm and a plurality of grasping arms rotatably coupled to the cutting arm. The grasping arms are connected to the cutting arm via a central hinge and are actuatable between a closed position against the cutting arm and an open position where the grasping arms extend laterally away from the cutting arm by rotating about the hinge. Targeted cardiac leaflet tissue may be grasped between the cutting arm and the grasping arms and cut by a cutting element that is attached to or extends through the cutting arm.

26 Claims, 13 Drawing Sheets

(51) Int. Cl.
- *A61B 17/29* (2006.01)
- *A61B 17/32* (2006.01)
- *A61B 17/34* (2006.01)
- *A61B 18/00* (2006.01)
- *A61B 18/14* (2006.01)
- *A61M 25/01* (2006.01)

(52) U.S. Cl.
CPC ..... *A61B 18/1492* (2013.01); *A61M 25/0136* (2013.01); *A61B 2017/00243* (2013.01); *A61B 2017/00783* (2013.01); *A61B 2017/2947* (2013.01); *A61B 2017/320052* (2013.01); *A61B 2018/00369* (2013.01); *A61B 2018/00601* (2013.01); *A61B 2018/1407* (2013.01); *A61B 2018/1412* (2013.01); *A61B 2018/144* (2013.01)

(58) Field of Classification Search
CPC .... A61B 17/3476; A61B 2017/320052; A61B 17/320016; A61B 2017/22097
See application file for complete search history.

(56) References Cited

U.S. PATENT DOCUMENTS

| | | |
|---|---|---|
| 2,108,206 A | 2/1938 | Mecker |
| 3,296,668 A | 1/1967 | Aiken |
| 3,378,010 A | 4/1968 | Codling et al. |
| 3,470,875 A | 10/1969 | Johnson |
| 3,557,780 A | 1/1971 | Sato |
| 3,671,979 A | 6/1972 | Moulopoulos |
| 3,675,639 A | 7/1972 | Cimber |
| 3,776,237 A | 12/1973 | Hill et al. |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,312,337 A | 1/1982 | Donohue |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,872,455 A | 10/1989 | Pinchuk et al. |
| 4,878,495 A | 11/1989 | Grayzel |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox et al. |
| 5,042,707 A | 8/1991 | Taheri |
| 5,047,041 A | 9/1991 | Samuels |
| 5,049,153 A | 9/1991 | Nakao et al. |
| 5,053,043 A | 10/1991 | Gottesman et al. |
| 5,061,277 A | 10/1991 | Carpentier et al. |
| 5,069,679 A | 12/1991 | Taheri |
| 5,071,428 A | 12/1991 | Chin et al. |
| 5,078,722 A | 1/1992 | Stevens |
| 5,078,723 A | 1/1992 | Dance et al. |
| 5,108,368 A | 4/1992 | Hammerslag et al. |
| 5,125,758 A | 6/1992 | Dewan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,217,460 A | 6/1993 | Knoepfler |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,336,227 A | 8/1994 | Nakao et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,373,854 A * | 12/1994 | Kolozsi ............... A61B 10/06 606/208 |
| 5,383,886 A | 1/1995 | Kensey et al. |
| 5,387,219 A | 2/1995 | Rappe |
| 5,391,182 A | 2/1995 | Chin |
| 5,395,030 A | 3/1995 | Kuramoto et al. |
| 5,403,312 A | 4/1995 | Yates et al. |
| 5,403,326 A | 4/1995 | Harrison et al. |
| 5,411,552 A | 5/1995 | Andersen et al. |
| 5,417,684 A | 5/1995 | Jackson et al. |
| 5,417,699 A | 5/1995 | Klein et al. |
| 5,417,700 A | 5/1995 | Egan |
| 5,423,830 A | 6/1995 | Schneebaum et al. |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,472,423 A | 12/1995 | Gronauer |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Karl-Dieter |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |

(56) References Cited

U.S. PATENT DOCUMENTS

| | | |
|---|---|---|
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,584,803 A | 12/1996 | Stevens et al. |
| 5,593,424 A | 1/1997 | Northrup, III |
| 5,593,435 A | 1/1997 | Carpentier et al. |
| 5,609,598 A | 3/1997 | Laufer et al. |
| 5,617,854 A | 4/1997 | Munsif |
| 5,618,306 A | 4/1997 | Roth et al. |
| 5,620,452 A | 4/1997 | Yoon |
| 5,620,461 A | 4/1997 | Muijs et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,669,919 A | 9/1997 | Sanders et al. |
| 5,690,671 A | 11/1997 | McGurk et al. |
| 5,695,504 A | 12/1997 | Gifford et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racenet et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,271 A | 4/1998 | Nakao et al. |
| 5,741,280 A | 4/1998 | Fleenor |
| 5,746,747 A | 5/1998 | McKeating |
| 5,749,828 A | 5/1998 | Yeung |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,591 A | 10/1998 | Thompson et al. |
| 5,820,592 A | 10/1998 | Hammerslag |
| 5,820,630 A | 10/1998 | Lind |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,103 A | 12/1998 | Wulfman |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson et al. |
| 5,895,404 A | 4/1999 | Ruiz |
| 5,895,417 A | 4/1999 | Pomeranz et al. |
| 5,906,620 A | 5/1999 | Nakao et al. |
| 5,908,420 A | 6/1999 | Parins et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhardt et al. |
| 5,957,973 A | 9/1999 | Quiachon et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,997,547 A | 12/1999 | Nakao et al. |
| 6,007,546 A | 12/1999 | Snow et al. |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,033,419 A | 3/2000 | Hamblin et al. |
| 6,036,699 A | 3/2000 | Andreas et al. |
| 6,048,351 A | 4/2000 | Gordon et al. |
| 6,053,933 A | 4/2000 | Balazs et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,090,118 A | 7/2000 | McGuckin, Jr. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,665 A | 9/2000 | Kawano |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,508 A | 10/2000 | Simpson et al. |
| 6,143,024 A | 11/2000 | Campbell et al. |
| 6,159,240 A | 12/2000 | Sparer et al. |
| 6,162,233 A | 12/2000 | Williamson et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,174,322 B1 | 1/2001 | Schneidt |
| 6,180,059 B1 | 1/2001 | Divino et al. |
| 6,182,664 B1 | 2/2001 | Cosgrove |
| 6,187,003 B1 | 2/2001 | Buysse et al. |
| 6,190,408 B1 | 2/2001 | Melvin |
| 6,197,043 B1 | 3/2001 | Davidson |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,264,617 B1 * | 7/2001 | Bales ............ A61B 10/06 600/564 |
| 6,267,746 B1 | 7/2001 | Bumbalough |
| 6,267,781 B1 | 7/2001 | Tu |

(56) References Cited

U.S. PATENT DOCUMENTS

| | | |
|---|---|---|
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,334,860 B1 | 1/2002 | Dorn |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,640 B1 | 7/2002 | Taylor |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,494,881 B1 | 12/2002 | Bales et al. |
| 6,508,828 B1 | 1/2003 | Akerfeldt et al. |
| 6,517,550 B1 | 2/2003 | Konya et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,921 B2 | 9/2003 | Blatter et al. |
| 6,626,930 B1 | 9/2003 | Allen et al. |
| 6,629,534 B1 | 10/2003 | St et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,932,810 B2 | 8/2005 | Ryan |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,056,294 B2 | 6/2006 | Khairkhahan et al. |
| 7,112,207 B2 | 9/2006 | Allen et al. |
| 7,226,467 B2 | 6/2007 | Lucatero et al. |
| 7,258,694 B1 | 8/2007 | Choi et al. |
| 7,288,097 B2 | 10/2007 | Seguin |
| 7,291,168 B2 | 11/2007 | Macoviak et al. |
| 7,338,467 B2 | 3/2008 | Lutter |
| 7,381,210 B2 | 6/2008 | Zarbatany et al. |
| 7,435,257 B2 | 10/2008 | Lashinski et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 7,955,340 B2 | 6/2011 | Michlitsch et al. |
| 8,216,234 B2 | 7/2012 | Long |
| 8,257,356 B2 | 9/2012 | Bleich et al. |
| 8,398,708 B2 | 3/2013 | Meiri et al. |
| 8,435,237 B2 | 5/2013 | Bahney |
| 8,496,655 B2 | 7/2013 | Epp et al. |
| 8,500,768 B2 | 8/2013 | Cohen |
| 8,523,881 B2 | 9/2013 | Cabiri et al. |
| 8,623,077 B2 | 1/2014 | Cohn |
| 8,690,858 B2 | 4/2014 | Machold et al. |
| 8,821,518 B2 | 9/2014 | Saliman et al. |
| 8,926,588 B2 | 1/2015 | Berthiaume et al. |
| 9,126,032 B2 | 9/2015 | Khairkhahan et al. |
| 9,211,119 B2 | 12/2015 | Hendricksen et al. |
| 9,370,341 B2 | 6/2016 | Ceniccola et al. |
| 9,498,331 B2 | 11/2016 | Chang et al. |
| 9,572,666 B2 | 2/2017 | Basude et al. |
| 9,770,256 B2 | 9/2017 | Cohen et al. |
| 9,949,833 B2 | 4/2018 | McCleary et al. |
| 10,238,493 B1 | 3/2019 | Metchik et al. |
| 10,667,804 B2 | 6/2020 | Basude et al. |
| 11,013,554 B2 | 5/2021 | Coates |
| 11,406,250 B2 | 8/2022 | Saadat et al. |
| 2001/0002445 A1 | 5/2001 | Vesely |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2001/0044635 A1 | 11/2001 | Niizeki et al. |
| 2002/0013547 A1 | 1/2002 | Paskar |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |

(56) References Cited

U.S. PATENT DOCUMENTS

| | | |
|---|---|---|
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030319 A1 | 2/2004 | Korkor et al. |
| 2004/0030382 A1 | 2/2004 | St et al. |
| 2004/0034380 A1 | 2/2004 | Woolfson et al. |
| 2004/0039442 A1 | 2/2004 | St et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059345 A1 | 3/2004 | Nakao et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0116951 A1 | 6/2004 | Rosengart |
| 2004/0122448 A1 | 6/2004 | Levine |
| 2004/0127849 A1 | 7/2004 | Kantor |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Liska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225233 A1 | 11/2004 | Frankowski et al. |
| 2004/0225300 A1 | 11/2004 | Goldfarb et al. |
| 2004/0225305 A1 | 11/2004 | Ewers et al. |
| 2004/0225353 A1 | 11/2004 | McGuckin et al. |
| 2004/0236354 A1 | 11/2004 | Seguin |
| 2004/0242960 A1 | 12/2004 | Orban |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Rahdert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St et al. |
| 2005/0021057 A1 | 1/2005 | St et al. |
| 2005/0021058 A1 | 1/2005 | Negro |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0065453 A1 | 3/2005 | Shabaz et al. |
| 2005/0085903 A1 | 4/2005 | Lau |
| 2005/0119735 A1 | 6/2005 | Spence et al. |
| 2005/0131438 A1 | 6/2005 | Cohn |
| 2005/0143809 A1 | 6/2005 | Salahieh et al. |
| 2005/0149014 A1 | 7/2005 | Hauck et al. |
| 2005/0159763 A1 | 7/2005 | Mollenauer et al. |
| 2005/0159810 A1 | 7/2005 | Filsoufi |
| 2005/0192633 A1 | 9/2005 | Montpetit |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | Demarchi et al. |
| 2005/0267493 A1 | 12/2005 | Schreck et al. |
| 2005/0273160 A1 | 12/2005 | Lashinski et al. |
| 2005/0277876 A1 | 12/2005 | Hayden |
| 2005/0287493 A1 | 12/2005 | Novak et al. |
| 2006/0004247 A1 | 1/2006 | Kute et al. |
| 2006/0009759 A1 | 1/2006 | Chrisitian et al. |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020334 A1 | 1/2006 | Lashinski et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0135993 A1 | 6/2006 | Seguin |
| 2006/0184198 A1 | 8/2006 | Bales et al. |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2006/0276890 A1 | 12/2006 | Solem et al. |
| 2007/0016225 A1 | 1/2007 | Nakao |

(56) References Cited

U.S. PATENT DOCUMENTS

| | | |
|---|---|---|
| 2007/0038293 A1 | 2/2007 | St et al. |
| 2007/0060997 A1 | 3/2007 | De Boer |
| 2007/0073185 A1* | 3/2007 | Nakao .................. A61B 10/06 606/205 |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0173757 A1 | 7/2007 | Levine et al. |
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2007/0287884 A1 | 12/2007 | Schena |
| 2008/0009858 A1 | 1/2008 | Rizvi |
| 2008/0039935 A1 | 2/2008 | Buch et al. |
| 2008/0045936 A1 | 2/2008 | Vaska et al. |
| 2008/0051703 A1 | 2/2008 | Thornton et al. |
| 2008/0051807 A1 | 2/2008 | St et al. |
| 2008/0097467 A1 | 4/2008 | Gruber et al. |
| 2008/0097489 A1 | 4/2008 | Goldfarb et al. |
| 2008/0167714 A1 | 7/2008 | St et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0243249 A1 | 10/2008 | Kohm et al. |
| 2008/0294175 A1 | 11/2008 | Bardsley et al. |
| 2008/0312496 A1 | 12/2008 | Zwolinski |
| 2009/0012538 A1 | 1/2009 | Saliman et al. |
| 2009/0036768 A1 | 2/2009 | Seehusen et al. |
| 2009/0156995 A1 | 6/2009 | Martin et al. |
| 2009/0163934 A1 | 6/2009 | Raschdorf et al. |
| 2009/0177266 A1 | 7/2009 | Powell et al. |
| 2009/0192510 A1 | 7/2009 | Bahney |
| 2009/0198322 A1 | 8/2009 | Deem et al. |
| 2009/0204005 A1 | 8/2009 | Keast et al. |
| 2009/0209955 A1 | 8/2009 | Forster et al. |
| 2009/0209991 A1 | 8/2009 | Hinchliffe et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St et al. |
| 2010/0022823 A1 | 1/2010 | Goldfarb et al. |
| 2010/0044410 A1 | 2/2010 | Argentine et al. |
| 2010/0121437 A1 | 5/2010 | Subramanian et al. |
| 2010/0152612 A1 | 6/2010 | Headley et al. |
| 2010/0217261 A1 | 8/2010 | Watson |
| 2010/0262231 A1 | 10/2010 | Tuval et al. |
| 2010/0268226 A1 | 10/2010 | Epp et al. |
| 2010/0298929 A1 | 11/2010 | Thornton et al. |
| 2011/0009864 A1 | 1/2011 | Bucciaglia et al. |
| 2011/0184405 A1 | 7/2011 | Mueller |
| 2011/0224710 A1 | 9/2011 | Bleich |
| 2011/0238052 A1 | 9/2011 | Robinson |
| 2012/0022527 A1 | 1/2012 | Woodruff et al. |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0157765 A1 | 6/2012 | Mitelberg |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0310330 A1 | 12/2012 | Buchbinder et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0109910 A1 | 5/2013 | Alexander et al. |
| 2013/0172828 A1 | 7/2013 | Kappel et al. |
| 2013/0317515 A1 | 11/2013 | Kuroda et al. |
| 2014/0039511 A1 | 2/2014 | Morris et al. |
| 2014/0135799 A1 | 5/2014 | Henderson |
| 2014/0228871 A1 | 8/2014 | Cohen et al. |
| 2014/0276913 A1 | 9/2014 | Tah et al. |
| 2014/0309670 A1 | 10/2014 | Bakos et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0364866 A1 | 12/2014 | Dryden et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0051698 A1 | 2/2015 | Ruyra et al. |
| 2015/0094800 A1 | 4/2015 | Chawla |
| 2015/0112430 A1 | 4/2015 | Creaven et al. |
| 2015/0211946 A1 | 7/2015 | Pons et al. |
| 2015/0230947 A1 | 8/2015 | Krieger et al. |
| 2015/0257877 A1 | 9/2015 | Hernandez |
| 2015/0257883 A1 | 9/2015 | Basude et al. |
| 2015/0306806 A1 | 10/2015 | Dando et al. |
| 2015/0313581 A1* | 11/2015 | Wolfe .................. A61B 10/06 600/567 |
| 2016/0015410 A1 | 1/2016 | Asirvatham et al. |
| 2016/0074165 A1 | 3/2016 | Spence et al. |
| 2016/0174979 A1 | 6/2016 | Wei |
| 2016/0317174 A1 | 11/2016 | Dake |
| 2017/0042678 A1 | 2/2017 | Ganesan et al. |
| 2017/0100183 A1 | 4/2017 | Iaizzo et al. |
| 2017/0143330 A1 | 5/2017 | Basude et al. |
| 2017/0202559 A1 | 7/2017 | Taha |
| 2017/0232238 A1 | 8/2017 | Biller et al. |
| 2018/0008268 A1 | 1/2018 | Khairkhahan |
| 2018/0028215 A1 | 2/2018 | Cohen |
| 2018/0092661 A1 | 4/2018 | Prabhu |
| 2018/0133010 A1 | 5/2018 | Kizuka |
| 2018/0161159 A1 | 6/2018 | Lee et al. |
| 2018/0360457 A1 | 12/2018 | Ellis et al. |
| 2019/0029790 A1 | 1/2019 | Bak-Boychuk et al. |
| 2019/0183571 A1 | 6/2019 | De Marchena |
| 2019/0298517 A1 | 10/2019 | Sanchez et al. |
| 2019/0307458 A1 | 10/2019 | Mathis et al. |
| 2020/0121460 A1 | 4/2020 | Dale et al. |
| 2021/0145574 A1 | 5/2021 | Childs et al. |

FOREIGN PATENT DOCUMENTS

| | | |
|---|---|---|
| CN | 103841899 A | 6/2014 |
| CN | 104244841 A | 12/2014 |
| DE | 3504292 C1 | 7/1986 |
| DE | 9100873 U1 | 4/1991 |
| DE | 10116168 A1 | 11/2001 |
| EP | 0179562 A1 | 4/1986 |
| EP | 0558031 A2 | 9/1993 |
| EP | 0684012 A2 | 11/1995 |
| EP | 0727239 A2 | 8/1996 |
| EP | 0782836 A1 | 7/1997 |
| EP | 1230899 A1 | 8/2002 |
| EP | 1674040 A2 | 6/2006 |
| EP | 1980288 A1 | 10/2008 |
| EP | 2005912 A2 | 12/2008 |
| EP | 2537487 A1 | 12/2012 |
| EP | 2641570 A1 | 9/2013 |
| EP | 2702965 A1 | 3/2014 |
| EP | 2740419 A1 | 6/2014 |
| EP | 3009103 A1 | 4/2016 |
| FR | 2705556 A1 | 12/1994 |
| FR | 2768324 A1 | 3/1999 |
| FR | 2903292 A1 | 1/2008 |
| GB | 1598111 A | 9/1981 |
| GB | 2151142 A | 7/1985 |
| JP | 09-253030 A | 9/1997 |
| JP | 11-089937 A | 4/1999 |
| JP | 2000-283130 A | 10/2000 |
| JP | 2001-517529 A | 10/2001 |
| JP | 2006-528911 A | 12/2006 |
| JP | 2013-516244 A | 5/2013 |
| JP | 2014-523274 A | 9/2014 |
| JP | 2015-502548 A | 1/2015 |
| JP | 2018-030008 A | 3/2018 |
| WO | 81/00668 A1 | 3/1981 |
| WO | 91/01689 A1 | 2/1991 |
| WO | 91/18881 A1 | 12/1991 |
| WO | 92/12690 A1 | 8/1992 |
| WO | 94/18881 A1 | 9/1994 |

(56) References Cited

FOREIGN PATENT DOCUMENTS

| | | |
|---|---|---|
| WO | 94/18893 A1 | 9/1994 |
| WO | 95/08292 A1 | 3/1995 |
| WO | 95/11620 A2 | 5/1995 |
| WO | 95/15715 A1 | 6/1995 |
| WO | 96/14032 A1 | 5/1996 |
| WO | 96/20655 A1 | 7/1996 |
| WO | 96/22735 A1 | 8/1996 |
| WO | 96/30072 A1 | 10/1996 |
| WO | 97/18746 A2 | 5/1997 |
| WO | 97/25927 A1 | 7/1997 |
| WO | 97/26034 A1 | 7/1997 |
| WO | 97/38748 A2 | 10/1997 |
| WO | 97/39688 A2 | 10/1997 |
| WO | 97/48436 A2 | 12/1997 |
| WO | 98/07375 A1 | 2/1998 |
| WO | 98/24372 A1 | 6/1998 |
| WO | 98/30153 A1 | 7/1998 |
| WO | 98/32382 A1 | 7/1998 |
| WO | 98/35638 A1 | 8/1998 |
| WO | 99/00059 A1 | 1/1999 |
| WO | 99/01377 A1 | 1/1999 |
| WO | 99/07295 A1 | 2/1999 |
| WO | 99/07354 A2 | 2/1999 |
| WO | 99/13777 A1 | 3/1999 |
| WO | 99/44524 A2 | 9/1999 |
| WO | 99/66967 A1 | 12/1999 |
| WO | 00/02489 A1 | 1/2000 |
| WO | 00/03651 A1 | 1/2000 |
| WO | 00/03759 A2 | 1/2000 |
| WO | 00/12168 A1 | 3/2000 |
| WO | 00/44313 A1 | 8/2000 |
| WO | 00/59382 A1 | 10/2000 |
| WO | 00/60995 A2 | 10/2000 |
| WO | 01/00111 A1 | 1/2001 |
| WO | 01/00114 A1 | 1/2001 |
| WO | 01/03651 A2 | 1/2001 |
| WO | 01/26557 A1 | 4/2001 |
| WO | 01/26586 A1 | 4/2001 |
| WO | 01/26587 A1 | 4/2001 |
| WO | 01/26588 A2 | 4/2001 |
| WO | 01/26703 A1 | 4/2001 |
| WO | 01/28432 A1 | 4/2001 |
| WO | 01/28455 A1 | 4/2001 |
| WO | 01/47438 A1 | 7/2001 |
| WO | 01/49213 A2 | 7/2001 |
| WO | 01/50985 A1 | 7/2001 |
| WO | 01/54618 A1 | 8/2001 |
| WO | 01/56512 A1 | 8/2001 |
| WO | 01/66001 A2 | 9/2001 |
| WO | 01/70320 A1 | 9/2001 |
| WO | 01/89440 A2 | 11/2001 |
| WO | 01/95831 A2 | 12/2001 |
| WO | 01/95832 A2 | 12/2001 |
| WO | 01/97741 A2 | 12/2001 |
| WO | 02/00099 A2 | 1/2002 |
| WO | 02/01999 A2 | 1/2002 |
| WO | 02/03892 A1 | 1/2002 |
| WO | 02/34167 A2 | 5/2002 |
| WO | 02/60352 | 8/2002 |
| WO | 02/62263 | 8/2002 |
| WO | 02/62270 | 8/2002 |
| WO | 02/62408 | 8/2002 |
| WO | 03/01893 A2 | 1/2003 |
| WO | 03/03930 | 1/2003 |
| WO | 03/20179 | 3/2003 |
| WO | 03/28558 A2 | 4/2003 |
| WO | 03/37171 | 5/2003 |
| WO | 03/47467 | 6/2003 |
| WO | 03/49619 | 6/2003 |
| WO | 03/73910 | 9/2003 |
| WO | 03/73913 | 9/2003 |
| WO | 03/82129 | 10/2003 |
| WO | 03/88809 A2 | 10/2003 |
| WO | 2003/105667 | 12/2003 |
| WO | 2004/004607 A1 | 1/2004 |
| WO | 2004/006810 A1 | 1/2004 |
| WO | 2004/012583 A2 | 2/2004 |
| WO | 2004/012789 A2 | 2/2004 |
| WO | 2004/014282 A2 | 2/2004 |
| WO | 2004/019811 A2 | 3/2004 |
| WO | 2004/030570 A2 | 4/2004 |
| WO | 2004/037317 A2 | 5/2004 |
| WO | 2004/045370 A2 | 6/2004 |
| WO | 2004/045378 A2 | 6/2004 |
| WO | 2004/045463 A2 | 6/2004 |
| WO | 2004/047679 A1 | 6/2004 |
| WO | 2004/062725 A1 | 7/2004 |
| WO | 2004/082523 A2 | 9/2004 |
| WO | 2004/082538 A2 | 9/2004 |
| WO | 2004/093730 A2 | 11/2004 |
| WO | 2004/103162 A2 | 12/2004 |
| WO | 2004/112585 A2 | 12/2004 |
| WO | 2004/112651 A2 | 12/2004 |
| WO | 2005/002424 A2 | 1/2005 |
| WO | 2005/018507 A2 | 3/2005 |
| WO | 2005/027797 A1 | 3/2005 |
| WO | 2005/032421 A2 | 4/2005 |
| WO | 2005/062931 A2 | 7/2005 |
| WO | 2005/112792 A2 | 12/2005 |
| WO | 2006/037073 A2 | 4/2006 |
| WO | 2006/105008 A1 | 10/2006 |
| WO | 2006/105009 A1 | 10/2006 |
| WO | 2006/113906 A1 | 10/2006 |
| WO | 2006/115875 A2 | 11/2006 |
| WO | 2006/115876 A2 | 11/2006 |
| WO | 2007/136829 A1 | 11/2007 |
| WO | 2008/103722 A2 | 8/2008 |
| WO | 2010/024801 A1 | 3/2010 |
| WO | 2010/121076 A2 | 10/2010 |
| WO | 2012/020521 A1 | 2/2012 |
| WO | 2013/049734 A1 | 4/2013 |
| WO | 2013/103934 A1 | 7/2013 |
| WO | 2014/064694 A2 | 5/2014 |
| WO | 2014/121280 A2 | 8/2014 |
| WO | 2016/022797 A1 | 2/2016 |
| WO | 2016/144708 A1 | 9/2016 |
| WO | 2016/150806 A1 | 9/2016 |
| WO | 2017/223073 A1 | 12/2017 |
| WO | 2018/009718 A1 | 1/2018 |
| WO | 2018/106482 A1 | 6/2018 |
| WO | 2018/236766 A1 | 12/2018 |
| WO | 2019/040943 A1 | 2/2019 |
| WO | 2019/195336 A1 | 10/2019 |

OTHER PUBLICATIONS

Abe et al, "De Vega's Annuloplasty for Acquired Tricuspid Disease: Early and Late Results in 110 Patients", Ann. Thorac. Surg., pp. 670-676, vol. 48 (Jan. 1989).

Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).

Agricola et al., "Mitral Valve Reserve in Double Orifice Technique: an Exercise Echocardiographic Study," Journal of Heart Valve Disease, 11(5):637-643 (2002).

Alfieri et al., "An Effective Technique to Correct Anterior Mitral Leaflet Prolapse," J. Card Surg., 14:468-470 (1999).

Alfieri et al., "Novel Suture Device for Beating Heart Mitral Leaflet Approximation," Annals of Thoracic Surgery, 74:1488-1493 (2002).

Alfieri et al., "The double orifice technique in mitral valve repair: a simple solution for complex problems," Journal of Thoracic and Cardiovascular Surgery, 122:674-681 (2001).

Alfieri et al., "The Edge to Edge Technique," The European Association for Cardio-Thoracic Surgery, 14th Annual Meeting, Frankfurt/ Germany, Oct. 7-11, 2000, Post Graduate Courses, Book of Proceedings.

Alfieri, "The Edge-to-Edge Repair of the Mitral Valve," [Abstract] 6th Annual New Era Cardiac Care: Innovation & Technology, Heart Surgery Forum, (Jan. 2003) pp. 103.

Ali Khan et al, Blade Atrial Septostomy: Experience with the First 50 Procedures, Cathet. Cardiovasc. Diagn., Aug. 1991, pp. 257-262, vol. 23.

(56) References Cited

OTHER PUBLICATIONS

Alvarez et al, Repairing the Degenerative Mitral Valve: Ten to Fifteen-year Follow-up, Journal Thoracic of Cardiovascular Surgery, Aug. 1996, pp. 238-247, vol. 112, No. 2.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.
Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al, Surgery for Acquired Heart Disease: Early Outcome of Mitral Valve Reconstruction in Patients with End-stage Cardiomyopathy, Journal of Thoracic and Cariovascular Surgery, Apr. 1995, pp. 676-683, vol. 109, No. 4.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dang N C et al., "Surgical Revision After Percutaneous Mitral Valve Repair with a Clip: Initial Multicenter Experience", The Annals of Thracic Surgery,Elsevier, United States, vol. 80, No. 6, pp. 2338-2342, (Dec. 1, 2005), XP027732951, ISSN:0003-4975 [retrieved on Dec. 1, 2005].
Dec et al, Idiopathic Dilated Cardiomyopathy, The New England Journal of Medicine, Dec. 8, 1994, pp. 1564-1575, vol. 331, No. 23.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Feldman, et al. Randomized Comparison of Percutaneous Repair and Surgery for Mitral Regurgitation: 5-Year Results of Everest II. J Am Coll Cardiol. Dec. 29, 2015;66(25):2844-2854.
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).

Frazier et al., #62 Early Clinical Experience with an Implantable, Intracardiac Circulatory Support Device: Operative Considerations and Physiologic Implications, 2003 STS Presentation, 1 page total. [Abstract Only].
Fucci et al, Improved Results with Mitral Valve Repair Using New Surgical Techniques, Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172 175.
Gatti et al., "The edge to edge technique as a trick to rescue an imperfect mitral valve repair," Eur. J. Cardiothorac Surg, 22:817-820 (2002).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al, Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade Atrial Septostomy; Experience with the First 50 Procedures", Catheterization and Cardiovascular Diagnosis, 23:257-262 (1991).
Kherani et al., "The Edge-To-Edge Mitral Valve Repair: The Columbia Presbyterian Experience," Ann. Thorac. Surg., 78:73-76 (2004).
Kron et al., "Surgical Relocation of the Posterior Papillary Muscle in Chronic Ischemic Mitral Regurgitation," Annals. of Thoracic Surgery, 74:600-601 (2002).
Park et al, Clinical Use of Blade Atrial Septostomy, Circulation, 1978, pp. 600-608, vol. 58.
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al, Linear Segmental Annuloplasty for Mitral Valve Repair, Ann. Thorac. Surg., Jan. 7, 1997, pp. 1805-1806, vol. 63.
Robicsek et al., #60 the Bicuspid Aortic Valve: How Does It Function? Why Does It Fail? 2003 STS Presentation, [Abstract Only].
Rose et al., "Late MitraClip Failure: Removal Technique for Leaflet-Sparing Mitral Valve Repair", Journal of Cardiac Surgery, (Jul. 4, 2012), XP055047339, DOI: 10.1111/j. 1540-8191.2012.01483.x [retrieved on Dec. 11, 2012].

(56) References Cited

OTHER PUBLICATIONS

Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Takizawa H et al: Development of a microfine active bending catheter equipped with MIF tactile sensors", Micro Electro Mechanical Systems, 1999. MEMS '99. Twelfth IEEE Interna Tional Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3."
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
U.S. Provisional Application filed Jul. 6, 2016, by Khairkhahan., U.S. Appl. No. 62/359,121.
U.S. Provisional Application filed Nov. 7, 2016, by Khairkhahan., U.S. Appl. No. 62/418,571.
U.S. Provisional Application filed Oct. 22, 2018, by Dale et al., U.S. Appl. No. 62/748,947.
Uchida et al, Percutaneous Cardiomyotomy and Valvulotomy with Angioscopic Guidance, Am. Heart J., Apr. 1991, pp. 1221-1224, vol. 121.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
U.S. Appl. No. 14/216,813, filed Mar. 17, 2014, Hernandez.
Votta et al., "3-D Computational Analysis of the Stress Distribution on the Leaflets after Edge-to-Edge Repair of Mitral Regurgitation," Journal of Heart Valve Disease, 11:810-822 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "The double-orifice technique for mitral valve reconstruction: predictors of postoperative outcome," Eur J. Cardiothorac Surg, 20:583-589 (2001).
Maisano et al, The Edge-to-edge Technique: A Simplified Method to Correct Mitral Insufficiency, Eur. J. Cardiothorac. Surg., Jan. 14, 1998, pp. 240-246, vol. 13.
Maisano et al, The future of transcatheter mitral valve interventions: competitive or complementary role of repair vs. replacement? Eur Heart J. Jul. 7, 2015; 36(26):1651-1659.
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The Future of Transcatheter Mitral Valve Interventions: Competitive or Complementary Role of Repair vs. Replacement?", Eur Heart J.36(26):1651-1659 ( Jul. 7, 2015 ).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, (1996) 10:867-873.
Mantovani et al., "Edge-to-edge Repair of Congenital Familiar Tricuspid Regurgitation: Case Report," J. Heart Valve Dis., 9:641-643 (2000).
McCarthy et al, "Tricuspid Valve Repair With the Cosgrove-Edwards Annuloplasty System", Ann. Thorac. Surg., 64:267-8 ( Jan. 16, 1997).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Repair With the Cosgrove-Edwards Annuloplasty System", Ann. Throac Surg. 64:267-8 (Jan. 16, 1997).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. 1):1-29-1-35 (2001).
Noera et al., "Tricuspid Valve Incompetence Caused by Nonpenetrating Thoracic Trauma", Annals of Thoracic Surgery, 51:320-322 (1991).
Notice of Allowance received for U.S. Appl. No. 14/216,787, filed Nov. 7, 2016.
Notice of Allowance received for U.S. Appl. No. 14/216,787, mailed on Nov. 7, 2016.
Notice of Allowance received for U.S. Appl. No. 14/577,852, filed Apr. 25, 2018.
Notice of Allowance received for U.S. Appl. No. 14/577,852, mailed on Apr. 25, 2018.
Notice of Allowance received for U.S. Appl. No. 15/642,245, mailed on Jan. 29, 2020.
Notice of Allowance received for U.S. Appl. No. 15/642,245, mailed on Mar. 27, 2020.
Notice of Allowance received for U.S. Appl. No. 15/642,245, mailed on Nov. 6, 2019.
Notice of Allowance received for U.S. Appl. No. 15/423,060, mailed on Jan. 27, 2020.
Office Action received for U.S. Appl. No. 14/216,787, filed Apr. 8, 2016.
Office Action received for U.S. Appl. No. 14/216,787, mailed on Apr. 8, 2016.
Office Action received for U.S. Appl. No. 14/216,813, filed Apr. 6, 2018.
Office Action received for U.S. Appl. No. 14/216,813, filed Dec. 15, 2017.
Office Action received for U.S. Appl. No. 14/216,813, filed Mar. 9, 2017.
Office Action received for U.S. Appl. No. 14/216,813, mailed on Apr. 6, 2018.
Office Action received for U.S. Appl. No. 14/216,813, mailed on Dec. 15, 2017.
Office Action received for U.S. Appl. No. 14/216,813, mailed on Mar. 9, 2017.
Office Action received for U.S. Appl. No. 14/577,852, filed May 16, 2017.

(56) References Cited

OTHER PUBLICATIONS

Office Action received for U.S. Appl. No. 14/577,852, filed Oct. 20, 2016.
Office Action received for U.S. Appl. No. 14/577,852, filed Sep. 7, 2017.
Office Action received for U.S. Appl. No. 14/577,852, mailed on May 16, 2017.
Office Action received for U.S. Appl. No. 14/577,852, mailed on Oct. 20, 2016.
Office Action received for U.S. Appl. No. 14/577,852, mailed on Sep. 7, 2017.
Office Action received for U.S. Appl. No. 15/423,060, mailed on Apr. 25, 2019.
Office Action received for U.S. Appl. No. 15/423,060, mailed on Aug. 19, 2019.
Office Action received for U.S. Appl. No. 15/423,060, mailed on Oct. 28, 2019.
Office Action received for U.S. Appl. No. 15/642,245, mailed on Aug. 9, 2019.
Office Action received for U.S. Appl. No. 15/724,545, filed Dec. 27, 2019.
Office Action received for U.S. Appl. No. 15/724,545, mailed on Dec. 27, 2019.
Office Action received for U.S. Appl. No. 15/724,545, mailed on May 1, 2020.
Osawa et al., "Partial Left Ventriculectomy in a 3-Year Old Boy with Dilated Cardiomyopathy," Japanese Journal of Thoracic and Cardiovascular Surg, 48:590-593 (2000).

\* cited by examiner

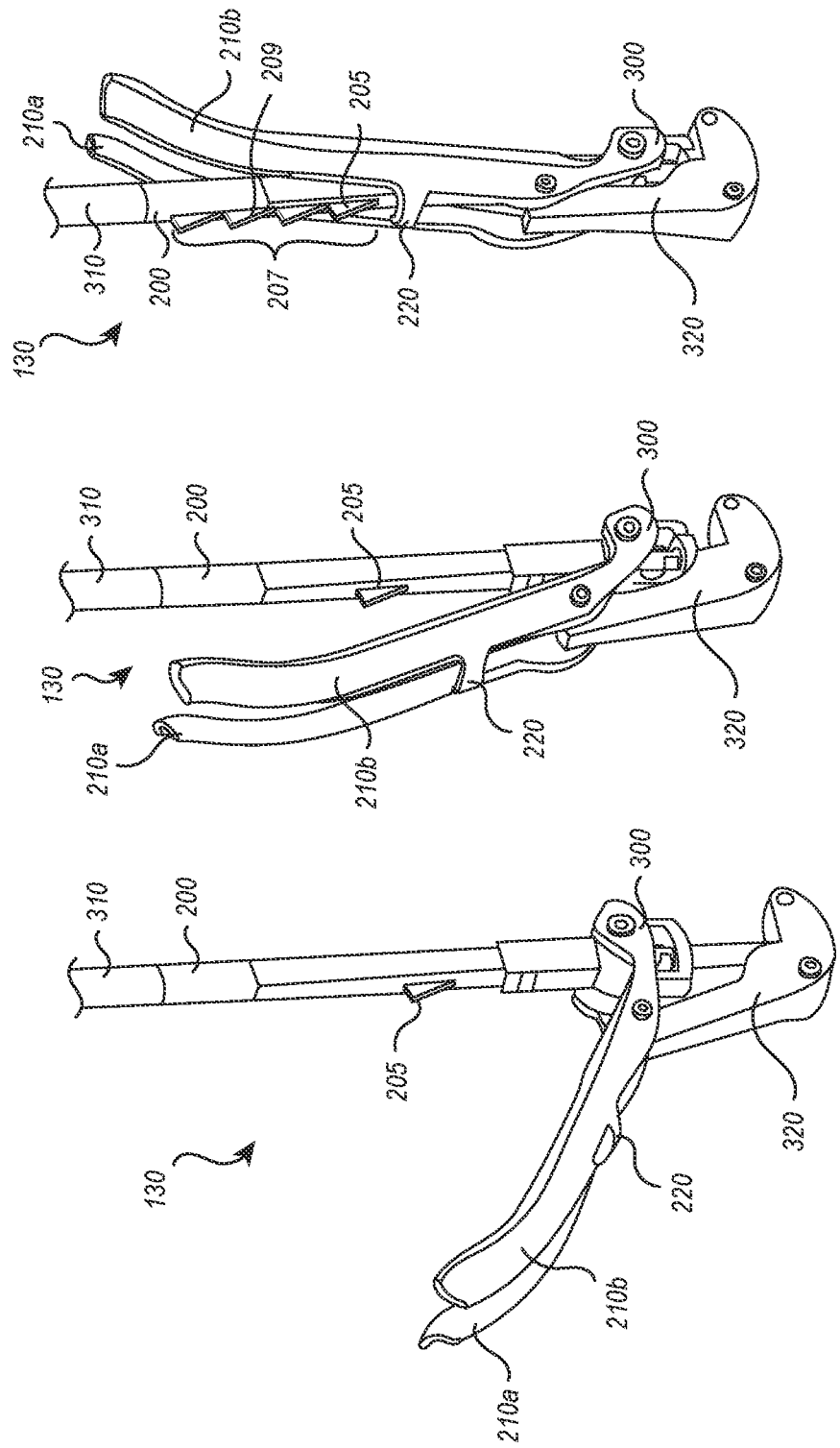

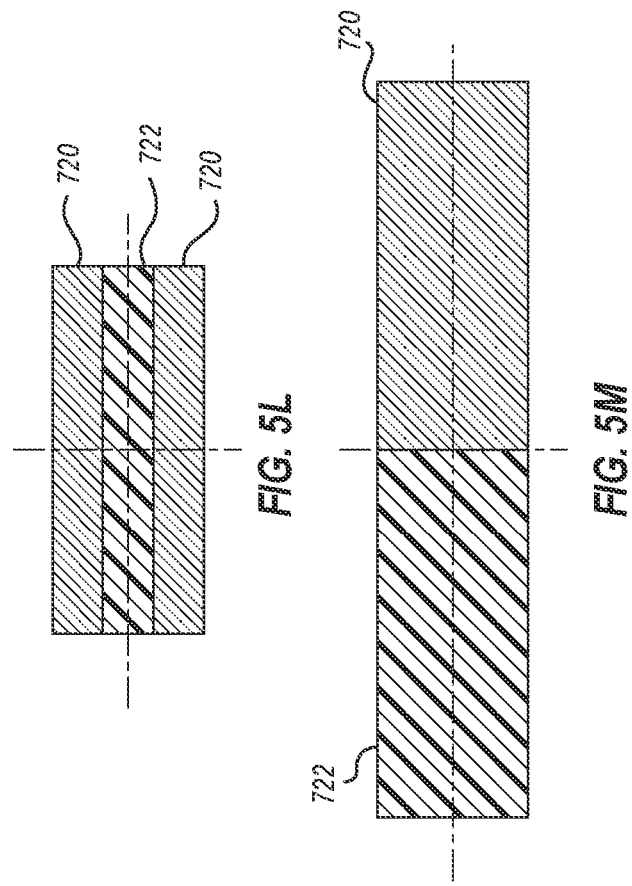
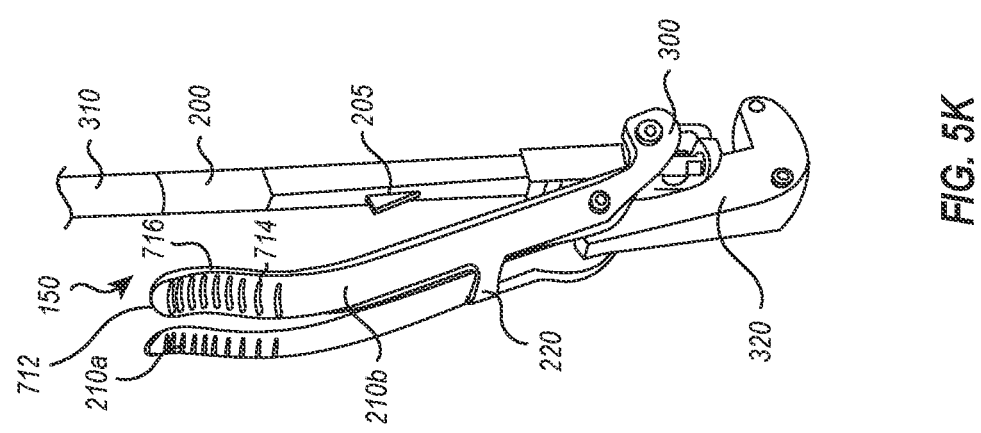

LEAFLET GRASPING AND CUTTING DEVICE

CROSS-REFERENCE TO RELATED APPLICATIONS

This application claims priority to U.S. Provisional Patent Application No. 63/020,662, filed May 6, 2020, the entire contents of which are incorporated by reference herein.

BACKGROUND OF THE INVENTION

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium.

Mitral valve regurgitation has several causes. Functional mitral valve regurgitation is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bowtie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity. In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, California, USA.

However, sometimes after a fixation device is installed, undesirable mitral valve regurgitation can still exist, or can arise again. For these sub-optimally treated patients, the presence of a fixation device in their mitral valves may obstruct additional procedures such as transcatheter mitral valve replacement. These patients may also be considered too frail to tolerate open-heart surgery, so they are often left with no viable options to further improve the function of their mitral valve.

Accordingly, it would be desirable to provide alternative and additional methods, devices, and systems for removing and/or disabling fixation devices that are already installed. At least some of these objectives will be met by the inventions described below.

BRIEF SUMMARY

The present disclosure is directed to systems, methods, and devices configured to effectively cut leaflet tissue at a cardiac valve and thereby enable removal of a cardiac valve fixation device and/or further interventional procedures involving the cardiac valve, such as implantation of a replacement valve.

In one embodiment, a cutting mechanism includes a cutting arm having a length extending along a longitudinal axis, the cutting arm including an actuatable cutting element configured to cut targeted leaflet tissue upon sufficient contact with the targeted leaflet tissue. The cutting mechanism further includes a central hinge disposed at or near a distal end of the cutting arm. One or more grasping arms are connected to the central hinge and each extend therefrom to a respective free end. The one or more grasping arms are rotatable about the central hinge so as to be selectively moveable between a closed position in which the one or more grasping arms are closed substantially against the cutting arm and an open position in which the one or more grasping arms are opened laterally away from the cutting arm. The cutting mechanism is configured to enable grasping of leaflet tissue between the cutting arm and the one or more grasping arms and to enable the cutting of grasped leaflet tissue via actuation of the cutting element.

An embodiment of a system for cutting leaflet tissue at a cardiac valve includes a guide catheter having a proximal end and a distal end, wherein the distal end of the guide catheter is steerable to a position above a cardiac valve, and a cutting mechanism. The cutting mechanism is routable through the guide catheter and configured to extend beyond the distal end of the guide catheter. The cutting mechanism is configured to enable grasping of leaflet tissue between the cutting arm and the one or more grasping arms and to enable the cutting of grasped leaflet tissue via actuation of the cutting element.

An embodiment of a method of cutting leaflet tissue at a cardiac valve within a body includes the steps of providing a system for cutting leaflet tissue, positioning the guide catheter such that the distal end of the guide catheter is positioned near a targeted cardiac valve, extending the cutting mechanism beyond the distal end of the guide catheter, grasping targeted leaflet tissue between the cutting arm and the one or more grasping arms of the cutting mechanism, and actuating the cutting element of the cutting mechanism to cut the grasped leaflet tissue. The targeted cardiac valve may have a fixation device attached to adjacent leaflets of the cardiac valve.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 5A-5C are more detailed views of a cutting mechanism according to the present disclosure, showing actuation of grasping arms from an open position to a closed position;

FIG. 5K illustrates another embodiment of a cutting mechanism having an auxiliary arm for moving the cutting element in response to actuation of a control rod;

FIGS. 5L and 5M illustrate alternate cross-sectional views of an auxiliary arm for moving a cutting element of the cutting mechanism;

DETAILED DESCRIPTION

Introduction

Embodiments described herein are configured to effectively cut leaflet tissue at a cardiac valve and thereby enable removal of a cardiac valve fixation device and/or enable further interventional procedures involving the cardiac valve, such as implantation of a replacement valve.

Figure 1:
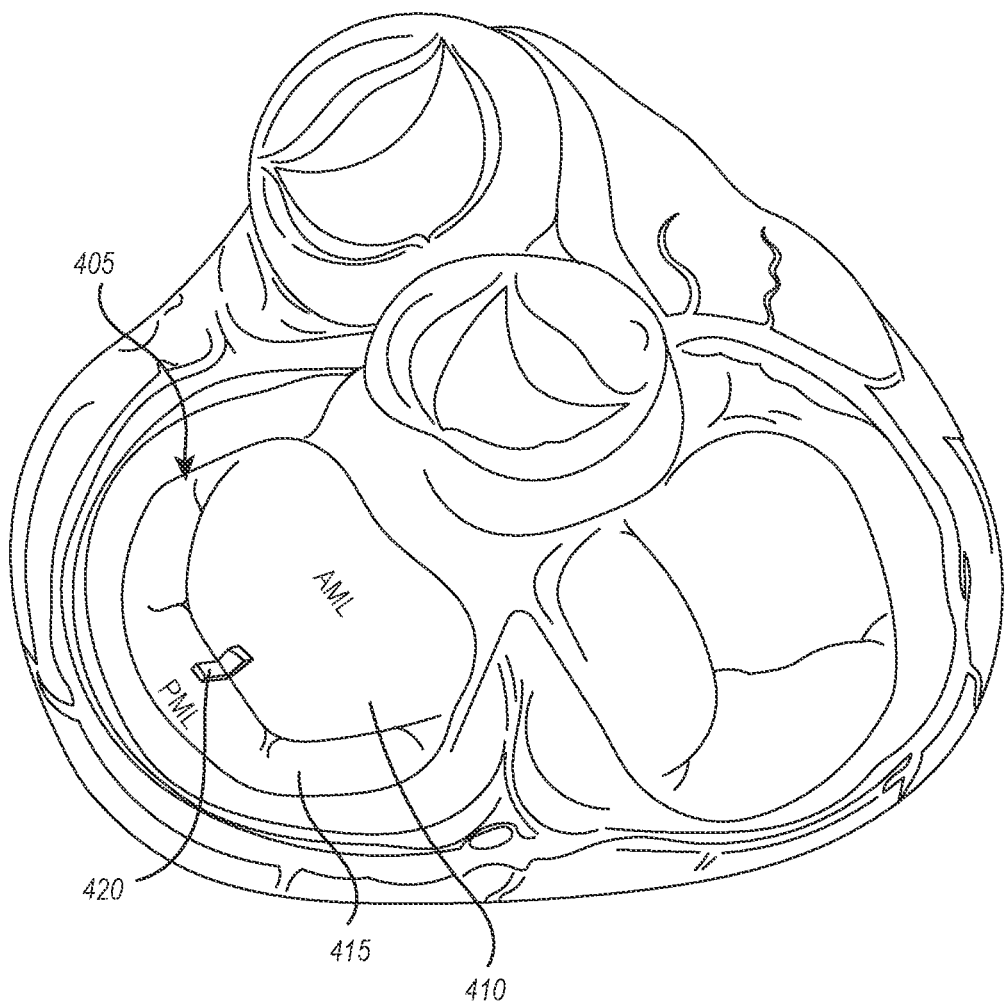
FIG. 1 illustrates a cross-sectional view of a human heart from a superior perspective, showing the mitral valve with an implanted clip fixation device for holding anterior and posterior leaflets of the mitral valve together.

FIG. 1 illustrates a cross-sectional view of a human heart from a superior perspective, showing the mitral valve 405, which includes an anterior leaflet 410 and a posterior leaflet 415. A clip fixation device 420 has been positioned in the mitral valve 405 to clip and hold the leaflets 410 and 415 together at the coapting edges. As explained above, such repair devices are often placed with the intent of reducing mitral valve regurgitation. However, if excessive regurgitation remains following placement of the device 420, or if excessive flow obstruction develops (mitral stenosis), and further interventional procedures are necessary or desired, the fixation device 420 may need to be detached from leaflet tissue and/or removed from the mitral valve 405. For example, the fixation device 420 may need to be repositioned or removed prior to the placement of a replacement valve.

Conventional techniques for cutting leaflet tissue to remove fixation devices include using a snare wire segment energized with radiofrequency (RF) energy to cut leaflet tissue surrounding the fixation device. However, such techniques suffer from drawbacks such as difficulty in clearly visualizing the anterior leaflet 410. Typically, cutting of the anterior leaflet 410 and not the posterior leaflet 415 is desired, because cutting of the posterior leaflet 415 can result in the free fixation device 420 and anterior leaflet 410 descending into the left ventricle and obstructing the left ventricular outflow tract (LVOT).

Conventional approaches also risk snaring sub-valvular anatomic structures such as mitral valve chordae tendineae or papillary muscles. Snaring and/or cutting these structures can result in damage to ventricular health and function. Snare wires may also become caught on or in between fixation devices prior to the application of RF energy, which can result in inadvertent transmittance of RF energy to the fixation device(s) (which typically include metal components). This can result in excessive heating in the heart, leading to localized tissue damage, tissue fragmentation and embolization, and excessive coagulation.

Embodiments described herein can provide several benefits to the art. For example, embodiments described herein may allow for the clear visualization of the anterior mitral leaflet during cutting in order to avoid inadvertently cutting the posterior mitral leaflet. Embodiments described herein are also configured to provide effective tissue grasping functionality that can minimize the risk of becoming caught or entangled with sub-valvular structures or the previously implanted fixation device(s). The structures and corresponding functions that enable such benefits are described in more detail below.

Although most of the following description will focus on cutting of the anterior mitral leaflet 410, it will be understood that the same components and features may be utilized, in some applications, to additionally or alternatively target the posterior mitral leaflet 415 for cutting. Further, although most of the examples describe the application of a cut that extends laterally across the anterior leaflet 410 (see FIGS. 8A-8D), the same components and features described herein may be utilized to cut a targeted leaflet radially rather than laterally. For example, in preparation for placement of a prosthetic replacement mitral valve, the anterior leaflet 410 may be cut radially to bisect the leaflet 410 and reduce the chance of outflow tract obstruction after a prosthetic replacement valve is implanted.

Moreover, although the examples described herein are provided in the context of cutting leaflet tissue of a mitral valve, one skilled in the art will appreciate that the embodiments described herein are not necessarily limited to use within the mitral valve 405. In other applications, the targeted cardiac valve could be the tricuspid valve, aortic valve, or pulmonic valve for example. More generally, the embodiments described herein may be utilized in other implementations involving removal of a previously implanted or deployed device from tissue.

In addition, although examples may illustrate routing the guide catheter to the mitral valve via a transfemoral/transseptal or transjugular/transseptal approach, other suitable delivery approaches may be used, including radial or transapical approaches.

Delivery System Overview

Figure 2:
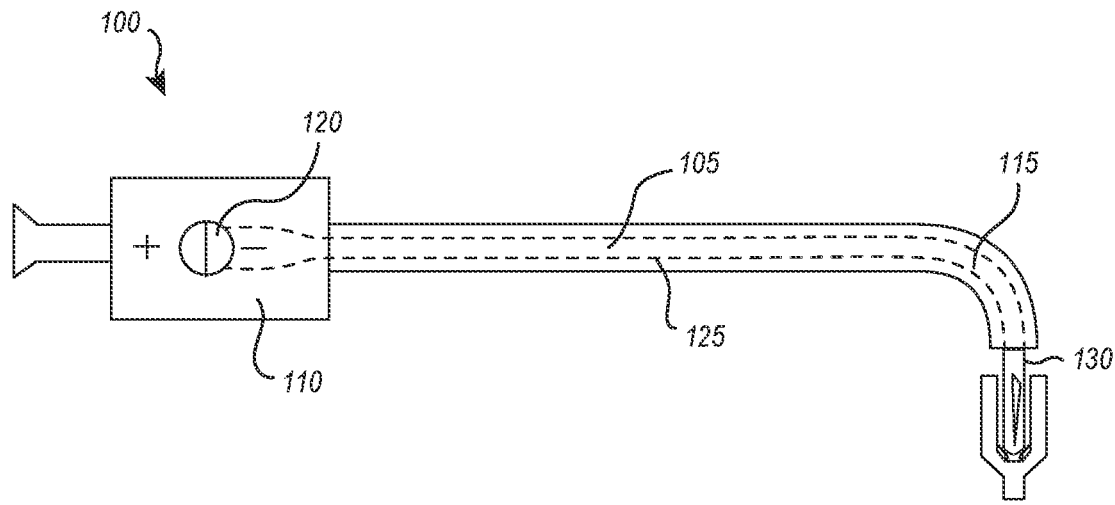
FIG. 2 illustrates an exemplary delivery system that may be utilized for guiding and/or delivering a cutting mechanism to a cardiac valve.

FIG. 2 illustrates an exemplary embodiment of a delivery system 100 that may be utilized for guiding and/or delivering a cutting mechanism 130 to a targeted cardiac valve. In at least one embodiment, the delivery system 100 includes a guide catheter 105 having a proximal end and a distal end 115. The delivery system may comprise a handle 110 positioned on the proximal end of the guide catheter 105. The guide catheter 105 may be operatively coupled to a handle 110. The guide catheter 105 may be steerable to enable the guiding and orienting of the guide catheter 105, including the distal end 115 of the guide catheter 105. For example, the handle 110 may include at least one control 120 (e.g., a dial, a switch, a slider, a button, etc.) that can be actuated to control the movement and curvature of the distal end 115 of the guide catheter 105.

As one example of a steering mechanism, the at least one control 120 may be operatively coupled to one or more control lines 125 (e.g., pull wires) extending from the handle 110 through the guide catheter 105 to the distal end 115 of the guide catheter (e.g., through one or more lumens in the guide catheter 105). Actuation of the at least one control 120 may adjust the tensioning of a control line 125 to pull the guide catheter 105 in the corresponding direction. FIG. 2 shows a pair of control lines 125. Alternatively, a handle 110 may comprise more than one control 120 configured for steering and any number of corresponding control lines. For example, the delivery system 100 may be configured to provide bending of the guide catheter 105 in multiple planes and/or at multiple bending points along the length of the guide catheter 105.

The control 120 and/or other controls disposed at the handle 110 may also be utilized to control actuation of various components of the cutting mechanism 130, as explained in more detail below. As shown in FIG. 2, the cutting mechanism 130 is configured in size and shape so as to be routable through the guide catheter 105 and extendable beyond the distal end 115 of the guide catheter 105. The cutting mechanism 130 may also be retracted back into the guide catheter 105. Control(s) 120 may control the cutting mechanism's 130 extension through and retraction back into the guide catheter 105. Additionally, or alternatively, the control(s) 120 may be configured to provide selective actuation of one or more components of the cutting mechanism 130.

Figure 3:
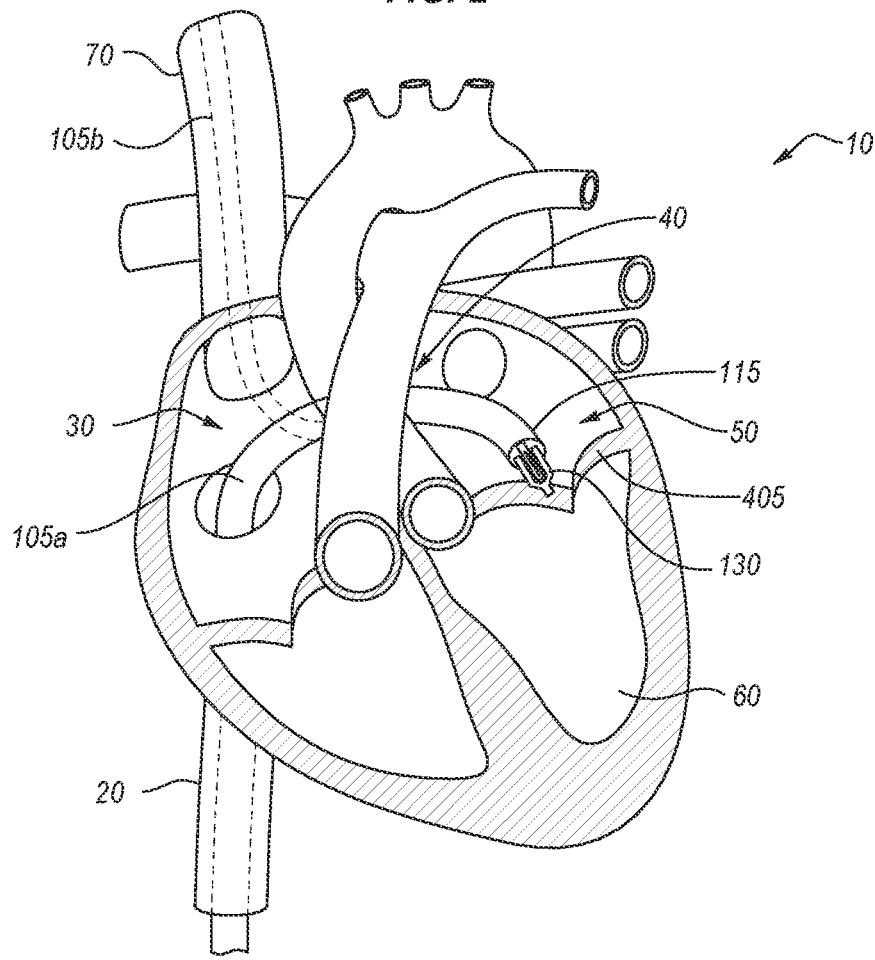
FIG. 3 is a perspective view of an exemplary embodiment of a cutting mechanism according to the present disclosure.

FIG. 3 illustrates a cross-sectional view of a patient's heart 10 from an anterior perspective, showing an exemplary approach for delivering the cutting mechanism to the targeted mitral valve 405 using the guide catheter 105. In particular, FIG. 3 illustrates a transfemoral approach via guide catheter 105 (shown for this approach as guide catheter 105a), and an alternative transjugular approach via guide catheter 105 (shown for this approach as guide catheter 105b).

In a transfemoral approach, the delivery catheter 105a is inserted into the patient's vasculature at a femoral vein and directed to the inferior vena cava 20. The catheter 105a is passed through the inferior vena cava 20 and into the right atrium 30. In the transjugular approach, the delivery catheter 105b is inserted into the patient's vasculature at a jugular vein and directed to the superior vena cava 70. The catheter 105b is passed through the superior vena cava 70 and into the right atrium 30. Subsequently, in either approach, the distal end 115 of the catheter is pushed across the septum 40 so as to be positioned in the left atrium 50 superior of the mitral valve 405.

As explained further below, the cutting mechanism 130 is then directed partially through the mitral valve 405 and partially into the left ventricle 60 so that leaflet tissue can be grasped and cut.

Cutting Mechanism Details

Figure 4:
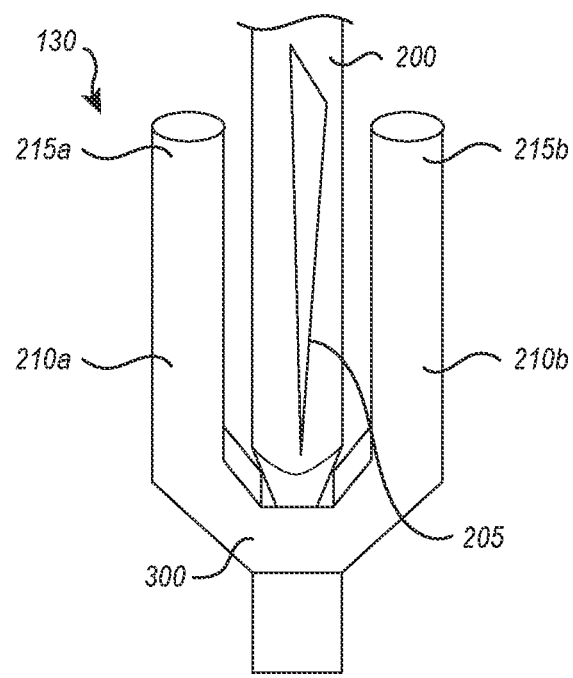
FIG. 4 illustrates a cross-sectional view of a human heart from an anterior perspective showing exemplary approaches for positioning a cutting mechanism at a targeted cardiac valve for cutting leaflet tissue therein.

FIG. 4 is an expanded view of the cutting mechanism 130. As shown, the cutting mechanism 130 may comprise a cutting arm 200 surrounded by at least two grasping arms 210a and 210b. The cutting mechanism 130 includes a central hinge 300 disposed at the distal end of the device. The grasping arms 210a and 210b connect to the cutting arm 200 at the central hinge 300 and extend therefrom to respective free ends 215a and 215b.

The grasping arms 210a and 210b may comprise a rigid, semi-rigid, or flexible material. Preferably, at least the tips of the grasping arms 210a and 210b near the free ends 215a and 215b may comprise a flexible material so they are atraumatic if contacted against the ventricular wall or subvalvular structures.

The grasping arms 210a and 210b may have a length of about 4 to about 40 mm, more typically about 6 to about 20 mm, although smaller or longer lengths may be utilized according to particular application needs. In at least one embodiment, the length of the at least two grasping arms 210a and 210b is adjustable.

FIG. 4 further shows that the cutting mechanism 130 may comprise a cutting element 205. The cutting element 205 may be configured to cut a portion of a leaflet grasped by the cutting mechanism 130 when the cutting mechanism 130 is actuated. In at least one embodiment, the cutting element 205 is spring loaded and/or configured to retract into the cutting arm 200 when not in use.

The cutting element 205 may comprise a sharpened edge, such as a mechanical blade, as shown in FIG. 4. Additionally, or alternatively, the cutting element 205 may comprise a tapered needle, an active electrosurgical electrode blade configured to provide radio frequency current energy to the portion of the leaflet, a wire loop, or other suitable structure capable of cutting leaflet tissue grasped by the cutting mechanism 130.

The cutting element 205 may have a length of at least the majority of the length of the cutting arm 200 in order to enable more expedient cutting of the leaflets. In other embodiments, the cutting element may have a length of less than the majority of the length of the cutting arm 200, in order to provide precise cutting and reduce the risk of inadvertent cutting of incorrect tissue.

In some embodiments, the cutting element 205 is disposed within the cutting arm 200. For example, the cutting arm 200 may comprise a slot through which the cutting element passes 205. The slot may have a greater length than the cutting element 205 to allow the cutting element 205 to move proximally/distally relative to the cutting arm 200, such as in a reciprocating motion, to aid in cutting grasped leaflet tissue.

The cutting arm 200 may comprise a gripping element configured to aid in gripping leaflet tissue in contact with the cutting arm 200. For example, the cutting arm 200 may include tines, barbs, one or more coatings, grooves, textured surfaces, and/or other features for increasing the friction of the cutting arm surface to prevent grasped tissue from sliding proximally and/or away from the cutting arm 200.

FIGS. 5A-5C illustrate the exemplary cutting mechanism 130 in greater detail, showing actuation and movement of the grasping arms 210a and 210b between an open position and a closed position. FIG. 5A shows the grasping arms 210a and 210b in an open position, FIG. 5B shows the grasping arms 210a and 210b in an intermediate position, and FIG. 5C shows the grasping arms 210a and 210b in a closed position.

FIGS. 5A-5C show that the grasping arms 210a and 210b may rotate laterally away from the cutting arm 200 by way of the central hinge 300. In a typical tissue grasping maneuver, the grasping arms 210a and 210b are opened to an angle of about 30 to about 60 degrees (such as shown in FIG. 5A), though the grasping arms 210a and 210b may be configured to open to an angle of up to about 90 degrees.

The cutting mechanism 130 may include a control rod 310 that extends through the cutting arm 200 (or runs parallel with it) to mechanically couple to a linkage assembly 320 of the cutting mechanism 130. The linkage assembly 320 is in turn mechanically connected to the grasping arms 210a and 210b. The control rod 310 is able to move in the axial direction relative to the cutting arm 200. A proximal end (not shown) of the control rod 310 can extend to the handle 110 and be operatively connected to one or more controls 120 (see FIG. 2).

Actuation of the control rod 310 moves the control rod 310 axially relative to the cutting arm 200 to thereby mechanically adjust the linkage assembly 320. Because the linkage assembly 320 is connected to the grasping arms 210a and 210b, the axial movement of the control rod 310 thereby controls rotation of the grasping arms 210a and 210b towards and away from the cutting arm 200. For example, the control rod 310 and linkage assembly 320 may be configured to move the grasping arms 210a and 210b toward the cutting arm 200 (and toward the closed position) when the control rod 310 is moved proximally relative to the cutting arm 200, and to move the grasping arms 210a and 210b away from the cutting arm 200 (and toward the open position) when the control rod 310 is moved distally relative to the cutting arm 200.

Other embodiments may additionally or alternatively include other actuation mechanisms for moving the cutting mechanism 130 between an open position and a closed position. For example, the cutting mechanism 130 may be configured to move between open and closed positions based on rotation of the control rod 310 and/or based on controlling tension in one or more control wires extending from the cutting mechanism 310 to one or more controls 120 of the handle 110. In some embodiments, the cutting mechanism 130 may be biased toward a "default" position (either the open position or the closed position), and once moved away from the default, biased position, a button, toggle, switch, or other control mechanism can be actuated to trigger release and rapid movement back to the default, biased position.

The shape and length of the at least two grasping arms 210a and 210b shown in FIGS. 5A-5C are merely exemplary. The at least two grasping arms 210a and 210b may be sized and shape to increase mechanical advantage of the at least two grasping arms 210a and 210b to exert tension on leaflet tissue grasped therebetween. In at least one embodiment the grasping arms 210a and 210b are configured to shield the cutting element 205 from surrounding cardiac structures. For example, a cover, webbing, or other protective structure may be positioned over the space between the grasping arms 210a and 210b to minimize the risk of the cutting element 205 inadvertently contacting anything not grasped between the cutting arm 200 and the grasping arms 210a and 210b.

As shown by the illustrated embodiment, the grasping arms 210a and 210b may have a curved profile to better position grasped tissue for cutting. For example, the free ends 215a and 215b may be curved inward toward the cutting arm 200. The free ends 215a and 215b may curve inwards at an angle of about 5 to about 20 degrees, for example, As shown in FIG. 5C, the grasping arms 210a and 210b may cross over the longitudinal axis of the cutting arm 200 as the grasping arms 210a and 210b move into the closed position, and this may be aided in part by the curved shape of the free ends 215a and 215b. This allows the cutting mechanism 130 to "over close" and better grasp and stretch leaflet tissue for more effective cutting of the leaflet tissue.

The shape of the cutting element 205 may be customized based on a patient's leaflet anatomy and pathology. Additionally, or alternatively, a cross bar 220 may be included partially connecting the two grasping arms 210a and 210b. The cross bar 220 may function to enhance tissue contact with the cutting arm 200 and/or cutting element 205, for example. As shown, the cross bar 220 may be disposed so as to be distal of the cutting element 205 (i.e., closer to the central hinge 300 than the cutting element 205) when the cutting mechanism 130 is in the closed position.

FIG. 5C illustrates an alternative configuration of cutting element 205, which includes a series of consecutive cutting elements 205 configured on the cutting arm 200. This configuration includes multiple cutting elements 205 can create a "serrated" blade 207, which can improve cutting performance while allowing the user to exert less than normal force during cutting. Normal force may be understood as the force used to make an adequate cut using a single cutting element 205. The dynamics of a beating heart can assist in accomplishing a full and clean cut against blade 207, which can be useful for removing stubborn pieces of leaflet tissue which might remain after an initial cutting attempt. If a strand of tissue remains, the beating of the heart can cause the strand of tissue to move or drag across the blade 27 in a dynamic way once its neighboring tissue is cut, which can subsequently aid in completion of the cut and removal of the strand of tissue. In some embodiments, all exposed cutting element edges 209 can be sharp to ensure bi-directional serrated cutting Alternatively, portions of the exposed cutting element edges 209 can be sharp.

The mitral and tricuspid valve leaflet tissue generally varies in thickness from ~0.4 mm thick for generally healthy tricuspid leaflet tissue, to ~3.2 mm for thick healthy mitral valve leaflet tissue. Diseased tissue may be thicker than healthy leaflet tissue as diseased tissue can be thickened to 5.0 mm and greater due to, for example, degenerative valve leaflet tissue or Barlow's disease. In some configurations, the cutting element 205 can be configured to cut to a depth sufficient to adequately cut through diseased tissue. A depth of the cutting element 205 can range from about 0.4 mm to about 10 mm, from about 0.5 mm to about 8 mm, from about 0.6 mm to about 4 mm, from about 0.8 mm to about 3 mm, from about 0.6 mm to about 10 mm, from about 0.8 mm to about 8 mm, from about 1 mm to about 4 mm, from about 1.2 mm to about 3 mm, and any combinations or modifications thereof. The cutting depth can be sufficient to cut through diseased tissue, while also shallow enough to avoid inadvertently cutting through tissue which should not be cut.

Figure 5F:
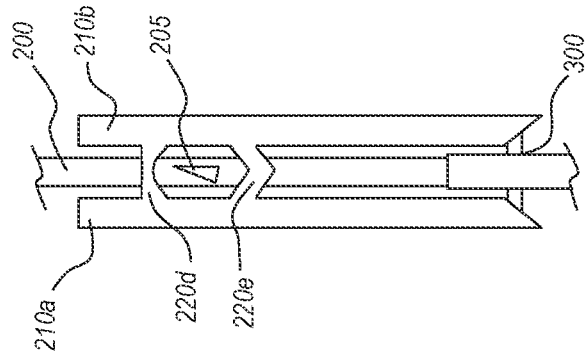
FIGS. 5D-5H illustrate exemplary configurations of the cutting mechanism of FIGS. 5A-5C including different cross bar orientations.
Figure 5E:
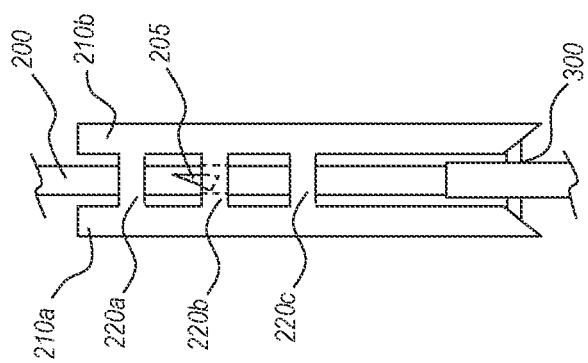
Figure 5D:
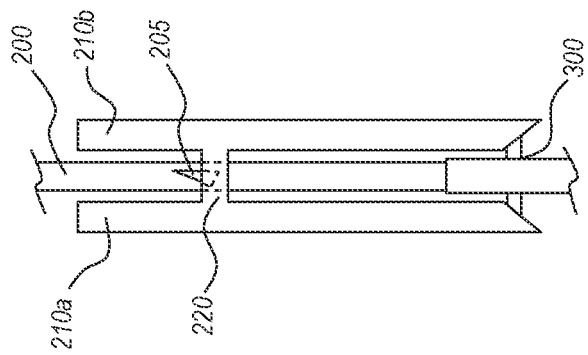

FIGS. 5D through 5H illustrate alternative configurations of the cross bar 220, grasping arms 210a, 210b, and the cutting element 205 that may be provided in addition to or as an alternative to the configuration shown in FIGS. 5A-5C. FIG. 5D illustrates that the cross bar 220 may be positioned so as to substantially align with the cutting element 205 when the cutting mechanism 130 is moved to the closed position. That is, the cross bar 220 may be positioned at the same location/height as the cutting element 205 so as to directly press tissue against the cutting element 205 when the cutting mechanism 130 moves into the closed position.

FIG. 5E illustrates that multiple cross bars 220 may be included (shown here as separate cross bars 220a through 220c). It will be appreciated that the cross bar(s) may be disposed at any of the locations along the lengths of the grasping arms 210a, 210b relative to the cutting element 205. For example, one or more cross bars 220a may be positioned above the cutting element 205 (i.e., farther from the central hinge 300 than the cutting element 205), one or more cross bars 220b may be substantially aligned with the cutting element 205, and/or one or more cross bars 220c may be positioned below the cutting element 205 (i.e., closer to the central hinge 200 than the cutting element 205).

Figure 5H:
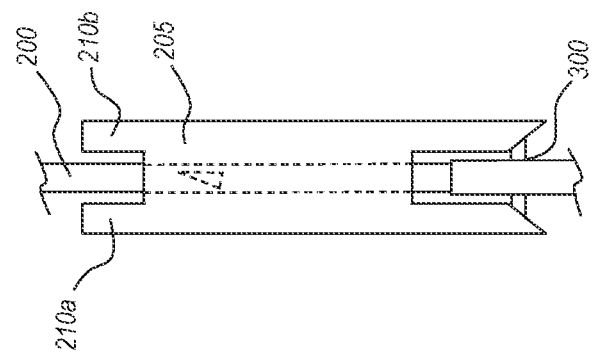
Figure 5G:
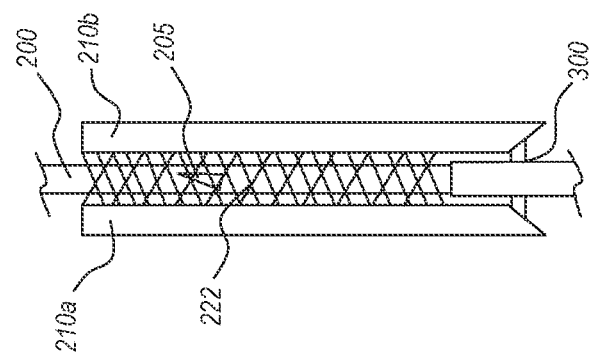

FIG. 5F illustrates that cross bars 220 need not necessarily be linearly disposed between the grasping arms 210a, 210b and may have, for example, a curved shape (such as cross bar 220d), angular shape (such as cross bar 220e), shape of variable width, or other non-linear and/or variable shape. FIG. 5G illustrates a configuration that includes a webbing 222 disposed between the grasping arms 210a and 210b. The webbing 222 may comprise a braided material, sheet, and/or film, for example, that extends across the gap between the grasping arms 210a and 210b. The webbing 222 may be formed to be cut-resistant or may be allowed to be cut along with tissue when the cutting element 205 is actuated. FIG. 5H illustrates a configuration where the gap between the grasping arms 210a and 210b is substantially filled so as to form a single, "solid" grasping arm structure. The grasping arm structure may have one or more grooves or indentations for receiving the cutting arm 200 and cutting element 205.

Figure 5I:
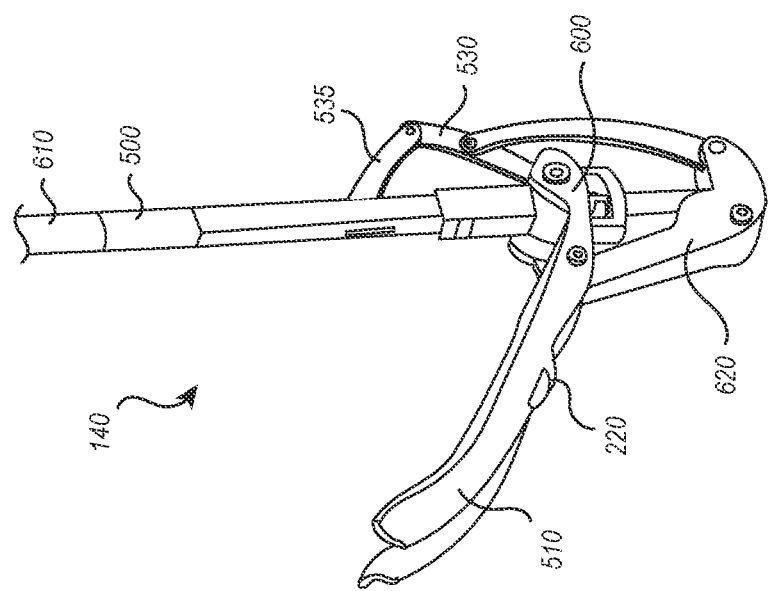
FIGS. 5I and 5J illustrate another embodiment of a cutting mechanism having an auxiliary arm for moving the cutting element in response to actuation of a control rod.
Figure 5J:
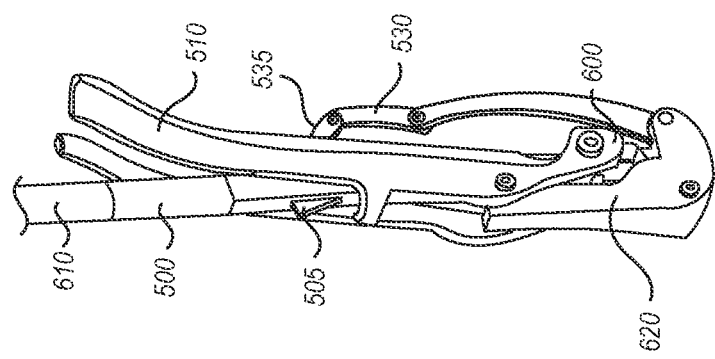

FIGS. 5I and 5J illustrates another embodiment of a cutting mechanism 140. The cutting mechanism 140, like the cutting mechanism 130 described above, may include a cutting arm 500, a cutting element 505, one or more grasping arms 510, a central hinge 600, a control rod 610, and a linkage assembly 620.

The cutting mechanism 140 additionally includes an auxiliary arm 530 disposed opposite the one or more grasping arms 510. The auxiliary arm 530 may be connected to the linkage assembly 620 and be configured to rotate about the central hinge 600 in response to controlled actuation via the control rod 610 in a fashion similar to the grasping arms 510. The auxiliary arm 530 includes a cutting element link 535 that connects to the cutting element 505. For example, the link 535 may extend through the cutting arm 500 to connect to the cutting element 505.

The auxiliary arm 530 can thus function to move the cutting element 505 in response to actuation (via axial movement) of the control rod 610. For example, actuation of the control rod 610 can cause the grasping arms 510 and the auxiliary arm 530 to move toward the closed position. As the auxiliary arm 530 closes and gets closer to the cutting arm 500, the link 535 pushes against the cutting element 505 and causes it to extend out from the cutting arm 500, as shown in FIG. 5E. Similarly, moving the grasping arms 510 and auxiliary arm 530 to the open position causes the cutting blade 505 to retract toward the cutting arm 500.

In use, the illustrated embodiment beneficially enables the cutting element 505 to be housed or substantially housed within the cutting arm 500 when the cutting mechanism 140 is in the open position, and enables the cutting element 505 to automatically extend and be exposed only as the grasping arms 510 are closing and targeted tissue is being brought into the cutting arm 500 to be cut.

As with the cutting element 205, the cutting element 505 can extend out from the cutting arm 500 a distance ranging from about 0.4 mm to about 10 mm, from about 0.5 mm to about 8 mm, from about 0.6 mm to about 4 mm, from about 0.8 mm to about 3 mm, from about 0.6 mm to about 10 mm, from about 0.8 mm to about 8 mm, from about 1 mm to about 4 mm, from about 1.2 mm to about 3 mm, and any combinations or modifications thereof. The cutting depth, or the distance which the cutting element 505 extends from the cutting arm 500 can be sufficient to cut through diseased tissue, while also shallow enough to avoid inadvertently cutting through tissue which should not be cut.

FIG. 5K illustrates another embodiment of a cutting element 150. The cutting mechanism 150, like the cutting mechanism 130 described above, may include a cutting arm 200, a cutting element 205, one or more grasping arms 210, a central hinge 300, a control rod 310, and a linkage assembly 320.

The cutting mechanism 150 additionally includes trauma reducing features. The grasping arms 210 which are used to press leaflet tissue into the cutting element 205 might become inadvertently caught on the patient's anatomy, so it may be useful to include trauma reducing features such as atraumatic tips 712 and flexibility-enhancing features, such as slit cuts 714. Other flexibility-enhancing features may include the grasping arms 210 having a tapered cross-section, and/or the grasping arms 210 may comprise multiple materials, with a more flexible material disposed towards the distal ends 716 of the grasping arms 210 to increase flexibility toward the distal ends 716 of the grasping arms 210. The multiple materials can include at least two metallic materials, at least two polymeric materials, at least one metallic material with at least one polymeric material, combinations or modifications thereof. For instance, one material can be over molded with another material. In another configuration, one material is bonded, glued, welded, brazed with or otherwise attached to another material.

The grasping arms 210 may still maintain their stiffness near the cutting element 205 to maintain their effectiveness, though by configuring the distal ends 716 of the grasping arms 210 to bend during use, damage to the leaflet tissue or chords can be minimized. The slit cuts 714 may be equally spaced along the distal ends 716 to impart an equal degree of flexibility along the distal ends 716. The slit cuts 714 may also be arranged in a pattern where the number and density of slit cuts 714 can increase towards the distal ends 716 to provide an increasing degree of flexibility towards the atraumatic tips 712. The pattern can include discrete or overlapping slits that are orientated parallel, perpendicular, and/or transverse to a longitudinal axis of a grasping arm 210.

The grasping arms 210 can comprise a metallic material such as steel, cobalt, chrome, NITINOL®, titanium, or the like, or a polymeric material, such as poly-L-lactide (PLLA), poly(lactic-co-glycolic acid) (PLGA), Polyether block amide (PEBA), such as PEBAX®, biocompatible composite, combinations and/or modifications thereof, or the like, or the grasping arms 210 can be a combination of a metallic material and a polymeric material. FIGS. 5L and 5M illustrate examples of various configurations of materials comprising the grasping arms 210 comprising material A 720 and material B 722. In some examples, material A 720 can comprise a metallic material or a polymeric material, as discussed above. Accordingly, material B 722 can comprise a metallic material or a polymeric material. Material A 720 and material B 722 are different materials and can be configured in a sandwich configuration as shown in FIG. 5L, or they can be arranged next to each other as shown in FIG.

5M. The materials can be arranged in a manner that imparts a desired stiffness and/or flexibility on the grasping arms 210.

Figure 5N:
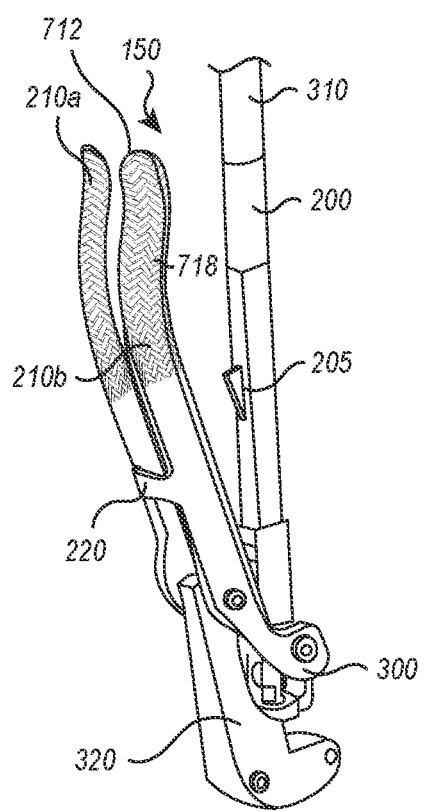
FIG. 5N illustrates another embodiment of a cutting mechanism having an auxiliary arm for moving the cutting element in response to actuation of a control rod.

All or a portion of each of the grasping arms 210 can also or alternatively have a braided structure 718, as illustrated in FIG. 5N, and may be laser cut from a tube or a sheet, or made from stamped or formed material. The braided structure 718 can have a larger, looser braid at the tips 712 in order to impart a desired degree of flexibility. The braided structure 718 can become progressively tighter woven and stiffer as the braided structure 718 progresses towards the middle of the grasping arms 210. The geometry of the grasping arms 210 as shown in FIGS. 5A-5K and 5N is curved with an inward bias towards the cutting arm 200, however, in some embodiments, the profile of the grasping arms 210 may be curved with an outward bias and flare outward relative to the cutting arm 200 in order to match the curvature of the leaflet tissue being cut.

Tissue Grasping & Cutting

Figure 6A:
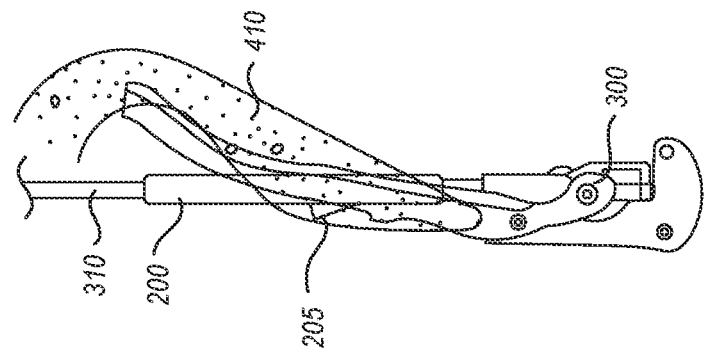
FIGS. 6A-6C illustrate the cutting mechanism of FIGS. 5A-5C while grasping leaflet tissue.
Figure 6B:
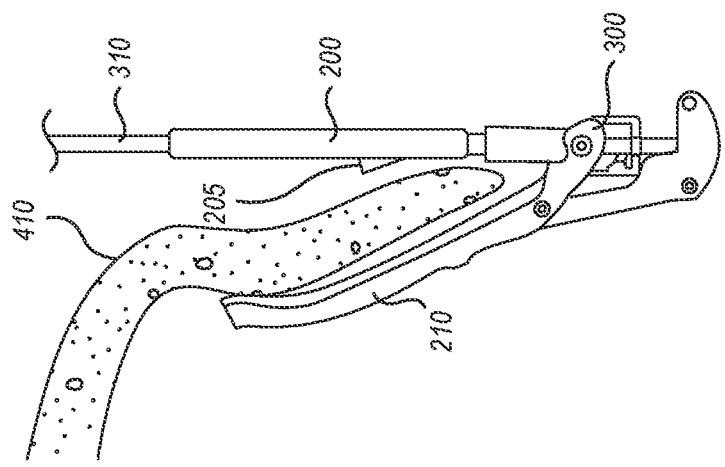
Figure 6C:
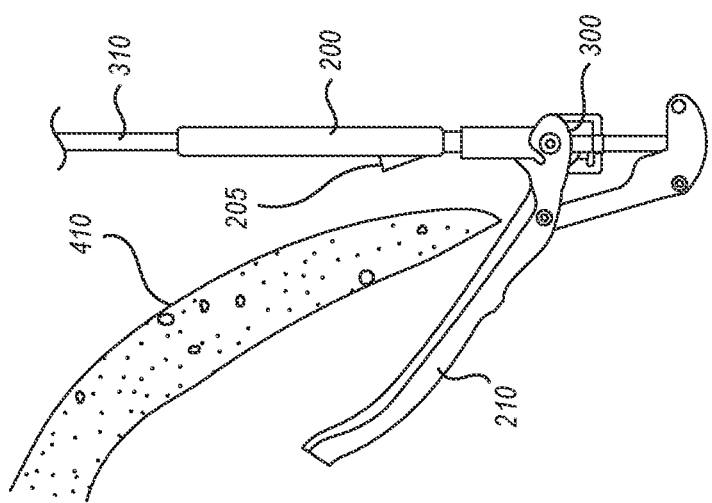

FIGS. 6A-6C illustrate additional views of the cutting mechanism 130 to show use of the cutting mechanism 130 to grasp and cut leaflet tissue (such as the anterior leaflet 410 shown here). Upon routing the cutting mechanism 130 to the appropriate position at the mitral valve, the cutting mechanism 130 may be moved from the closed position to the open position. Typically, the cutting mechanism 130 is positioned so that the grasping arms 210 are on the ventricular side of the valve, and then the cutting mechanism 130 is actuated to move the grasping arms 210 to the open position. As described above, the grasping arms 210 may be actuated by moving the control rod 310 axially relative to the cutting arm 200 to cause the linkage assembly 320 to rotate the grasping arms 210 outward.

FIG. 6A shows the cutting mechanism 130 in the open position (e.g., with the grasping arms 210 open to an angle of about 60 degrees) with the grasping arms 210 on the ventricular side of the leaflet 410. The cutting mechanism 130 may be moved to appropriately position the targeted leaflet 410 between the grasping arms 210 and the cutting arm 200. Then, as shown in FIG. 6B, the grasping arms 210 may be moved toward the closed position by axially moving the control rod 310 relative to the cutting arm 200. Further actuation leads to further closing of the grasping arms 210 until the leaflet 410 is brought into contact with the cutting element 205, as shown in FIG. 6C.

In some embodiments, the cutting element 205 is connected to the control rod 310, and the control rod 310 extends through the cutting arm 200. The cutting element 205 may pass through a slit in the cutting arm 200, for example. In such an embodiment, axial movement of the control rod 310 causes corresponding axial movement of the cutting element 205 relative to the cutting arm 200. This beneficially provides an axial cutting motion of the cutting element 205 while the grasping arms 210 are moving.

For example, moving the control rod 310 proximally may simultaneously close the grasping arms 210 and cause the cutting element 205 to move proximally, allowing for an effective cutting motion that simultaneously brings the leaflet 410 laterally into the cutting element 205 while axially moving the cutting element 205 to cut the leaflet 410. This can also be utilized to perform a "reciprocating cut" procedure where the cutting element 205 reciprocates axially while the grasping arms 210 are successively opened and closed to grasp new areas of leaflet tissue.

Figure 7A:
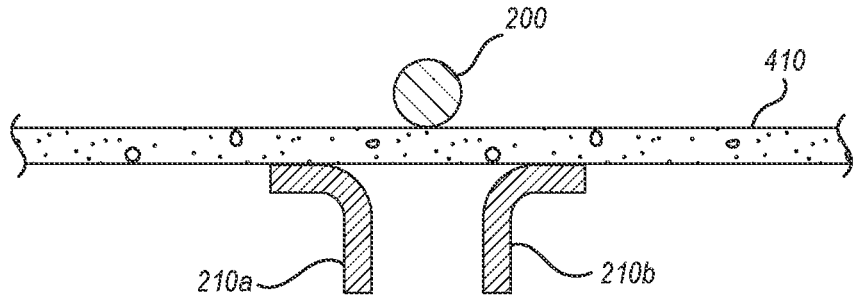
FIGS. 7A-7C illustrate a cross-sectional view of the cutting mechanism during grasping and cutting of leaflet tissue.
Figure 7B:
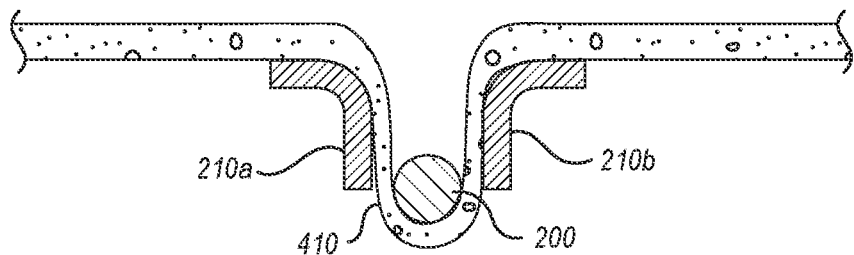
Figure 7C:
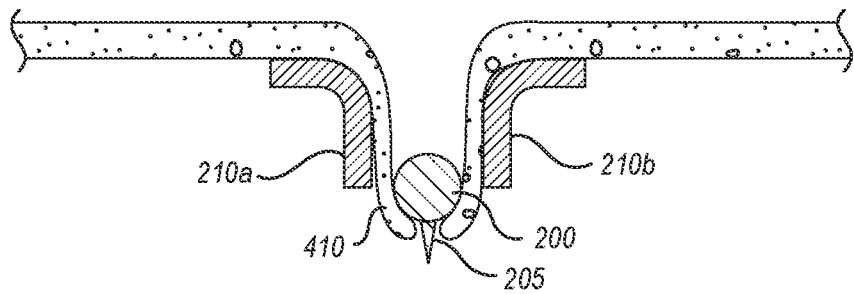
Figure 8A:
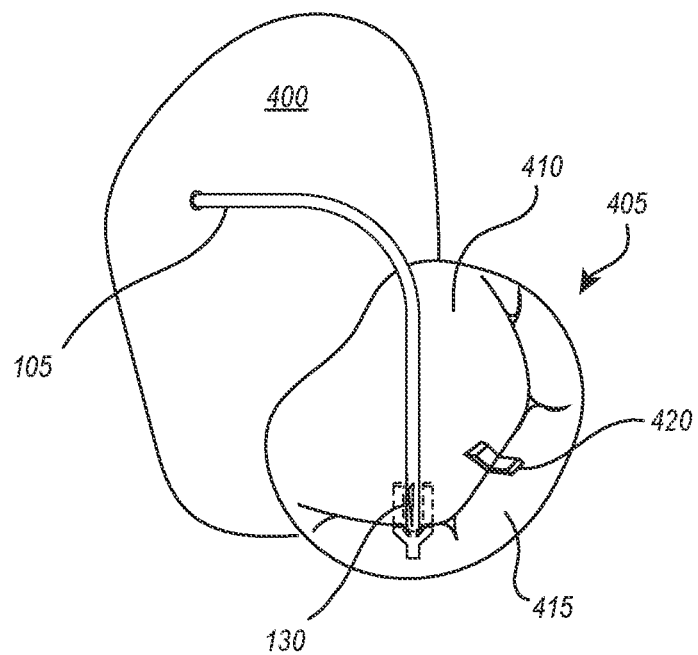
FIGS. 8A-8D illustrate delivery of the cutting mechanism to the mitral valve and use of the cutting mechanism to cut targeted leaflet tissue at the mitral valve.
Figure 8B:
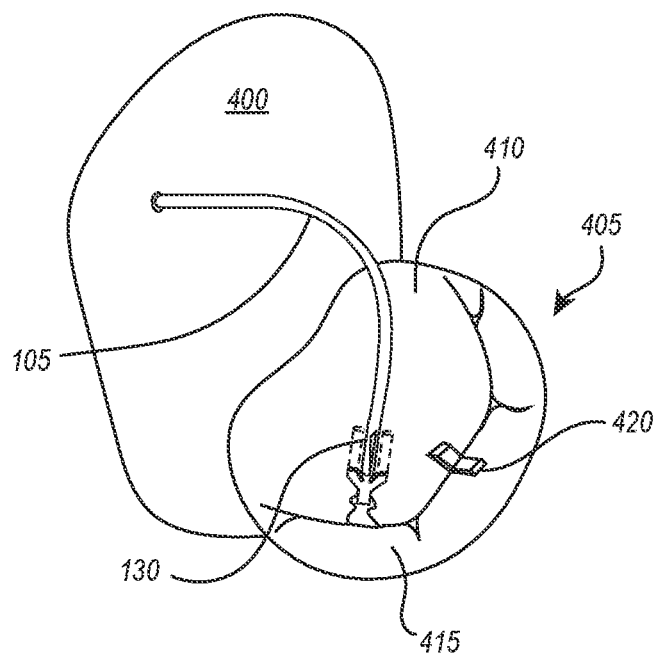
Figure 8C:
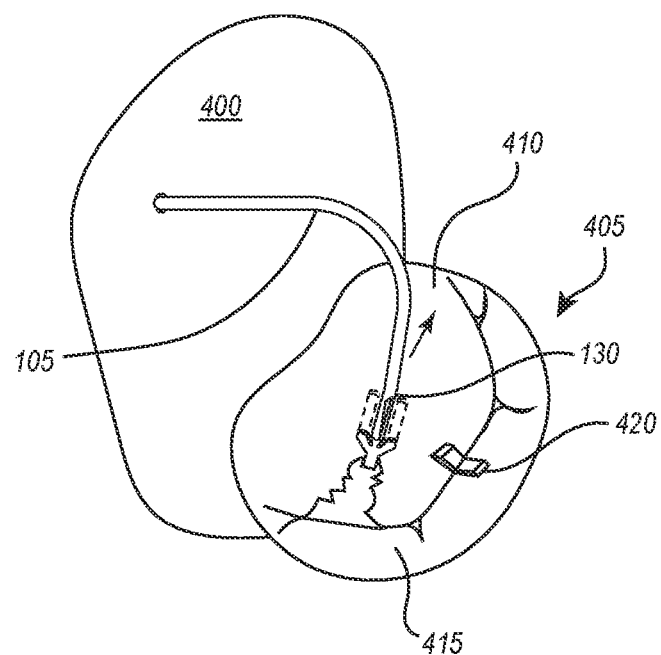
Figure 8D:
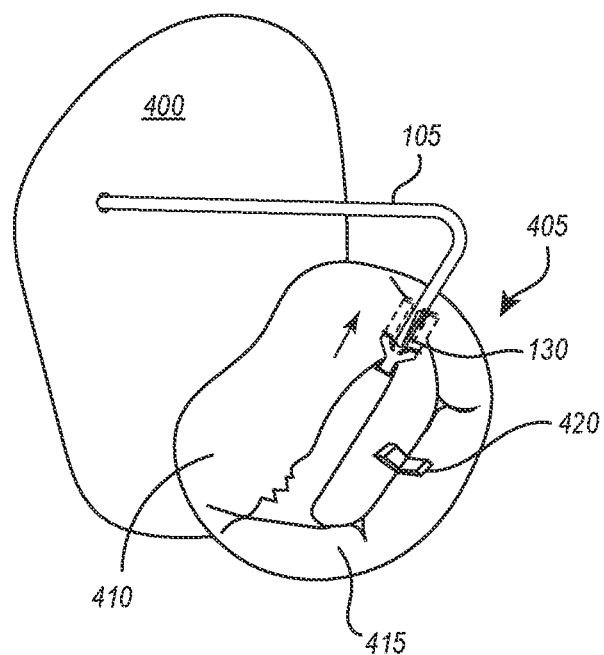

FIGS. 7A-7C illustrate the cutting element 130 while grasping and cutting leaflet tissue from a cross-sectional view across the longitudinal axis of the cutting mechanism.

FIGS. 7A-7C beneficially illustrate how the cutting element 130 may be utilized to stretch the grasped leaflet tissue (such as the anterior leaflet 410) across the cutting arm 200 for effective cutting of the tissue by the cutting element 205.

FIG. 7A shows the leaflet 410 disposed between the cutting arm 200 and the grasping arms 210a and 210b as the device approaches the closed position. FIG. 7B illustrates further closing of the grasping arms 210a and 210b such that the grasping arms 210a and 210b cross the longitudinal axis of the cutting arm 200 in an "over closed" fashion. This serves to tighten and stretch the grasped tissue across the cutting side of the cutting arm 200 so that it can be effectively cut by contact with the cutting element 205, as shown in FIG. 7C.

FIGS. 7A-7C also illustrate that the grasping arms 210a and 210b may have a curved or flared cross-sectional shape. Such a shape may correspond beneficially with the shape of the cutting arm 200 and may aid in providing the tightening and/or stretching of the grasped leaflet tissue across the cutting arm 200.

FIGS. 8A-8D are perspective views of the exemplary cutting mechanism 130 as used to cut leaflet tissue of the mitral valve 405. An interventional fixation device 420 creates a first and second orifice between the anterior mitral leaflet 410 and the posterior mitral leaflet 415 by approximating the adjacent leaflets 410 and 415. As shown, the distal end 115 of the guide catheter 105 has been extended through the septum 400 of the heart. The cutting mechanism 130 may be routed through the guide catheter 105 so as to extend through an orifice of the mitral valve 405 and be at least partially disposed on a ventricular side of the valve 405.

The grasping arms may then be actuated to move the cutting mechanism 130 to the open position. The cutting mechanism 130 is then positioned so that leaflet tissue, such as tissue of the anterior leaflet 410, resides between the grasping arms and the cutting arm. The cutting mechanism 130 is then moved to the closed position to grasp the leaflet tissue between the cutting arm and the grasping arms. The leaflet tissue may be secured by the grasping arms on a ventricular side of the mitral valve 405 and by the cutting arm on the atrial side of the mitral valve 405. With the application of some clamping force, the grasping arms can stretch the leaflet tissue across the cutting arm thereby reducing the thickness of the secured leaflet tissue at that location, and thereby better enable the cutting element to cut through the entire thickness of the secured leaflet tissue.

As shown in FIG. 4C, the cutting mechanism 130 may be advanced through the anterior mitral leaflet 410 by repeated repositioning of the cutting mechanism 130 and repeated actuation of the grasping arms. Additionally, or alternatively, the cutting mechanism 130 may be advanced through the anterior leaflet 410 by partially actuating the at least two grasping arms (e.g., to an open angle of about 15 to about 45 degrees), dynamically positioning the cutting mechanism 130, and moving or dragging the cutting mechanism 130 along the anterior mitral leaflet 410.

ADDITIONAL EXEMPLARY EMBODIMENTS

Following are some further example embodiments of the invention. These are presented only by way of example and are not intended to limit the scope of the invention in any way.

Embodiment 1. A cutting mechanism for cutting leaflet tissue at a cardiac valve, the cutting mechanism comprising: a cutting arm having a length extending along a longitudinal axis, the cutting arm including an actuatable cutting element configured to cut targeted leaflet tissue upon sufficient contact with the targeted leaflet tissue; a central hinge disposed at or near a distal end of the cutting arm; one or more grasping arms each connected to the central hinge and extending therefrom to a respective free end, the one or more grasping arms being rotatable about the central hinge so as to be selectively moveable between a closed position wherein the one or more grasping arms are closed substantially against the cutting arm, and an open position wherein the one or more grasping arms are opened laterally away from the cutting arm by rotating about the central hinge, wherein the cutting mechanism is configured to enable grasping of leaflet tissue between the cutting arm and the one or more grasping arms and to enable the cutting of grasped leaflet tissue via actuation of the cutting element.

Embodiment 2. The cutting mechanism of claim 1, wherein the cutting mechanism comprises at least two grasping arms disposed such that, when the cutting mechanism is in the closed position, a first grasping arm is disposed on a first side of the cutting arm and a second grasping arm is disposed on a second, opposite side of the cutting arm.

Embodiment 3. The cutting mechanism of Embodiment 2, wherein the cutting element is disposed on a portion of the cutting arm between the first and second grasping arms so as to enable cutting of leaflet tissue disposed between the first and second grasping arms.

Embodiment 4. The cutting mechanism of Embodiment 2 or Embodiment 3, further comprising a cross bar extending between the first and second grasping arms.

Embodiment 5. The cutting mechanism of Embodiment 4, wherein the cross bar is aligned with the cutting element when the cutting mechanism is in the closed position, or is positioned closer to the central hinge than the cutting element when the cutting mechanism is in the closed position.

Embodiment 6. The cutting mechanism of any one of Embodiments 1-5, wherein the one or more grasping arms are openable to an angle of up to about 90 degrees from the cutting arm.

Embodiment 7. The cutting mechanism of any one of Embodiments 1-6, wherein the free ends of the one or more grasping arms curve laterally inward toward the cutting arm.

Embodiment 8. The cutting mechanism of Embodiment 7, wherein the curved free ends of the one or more grasping arms cross over the longitudinal axis of the cutting arm when moving from the open position to the closed position.

Embodiment 9. The cutting mechanism of Embodiment 7 or Embodiment 8, wherein the curved free ends curve laterally inward at an angle of between about 5 degrees and about 20 degrees.

Embodiment 10. The cutting mechanism of any one of Embodiments 1-9, wherein the cutting element is spring-loaded so as to be capable of actuation from a non-deployed to a deployed state via controlled release of spring energy.

Embodiment 11. The cutting mechanism of any one of Embodiments 1-10, wherein the central hinge comprises a linkage mechanism configured to convert axial movement of a control rod along the longitudinal axis of the cutting arm into lateral movement of the grasping arms.

Embodiment 12. The cutting mechanism of Embodiment 11, wherein the cutting element is connected to the control rod and extends through a slot of the cutting arm such that actuation of the control rod moves the cutting element within the slot in an axial direction relative to the cutting arm.

Embodiment 13. The cutting mechanism of any one of Embodiments 1-12, wherein the one or more grasping arms have a length of about 4 mm to about 40 mm.

Embodiment 14. The cutting mechanism of any one of Embodiments 1-13, wherein the cutting element comprises a sharpened edge.

Embodiment 15. The cutting mechanism of any one of Embodiments 1-14, wherein the cutting element comprises a tapered needle.

Embodiment 16. The cutting element of any one of Embodiments 1-15, wherein the cutting element comprises a wire loop configured to provide radio frequency current energy.

Embodiment 17. The cutting element of any one of Embodiments 1-16, wherein the cutting arm includes a gripping element configured to aid in gripping leaflet tissue in contact with the cutting arm.

Embodiment 18. The cutting mechanism of any one of Embodiments 1-17, further comprising an auxiliary arm connected to the central hinge and disposed opposite the one or more grasping arms, the auxiliary arm being mechanically connected to the cutting element such that movement of the auxiliary arm as the cutting mechanism moves between the open position and the closed position causes advancement and retraction of the cutting element relative to the cutting arm.

Embodiment 19. The cutting mechanism of any of the Embodiments 1-18, wherein the cutting element comprises at least two or more cutting elements.

Embodiment 20. The cutting mechanism of any of the Embodiments 1-19, wherein the cutting element has a depth of about 0.4 mm to about 10 mm.

Embodiment 21. A system for cutting leaflet tissue at a cardiac valve, the system comprising: a guide catheter having a proximal end and a distal end, wherein the distal end of the guide catheter is steerable to a position above a cardiac valve; and a cutting mechanism as in any one of Embodiments 1-20 routable through the guide catheter and configured to extend beyond the distal end of the guide catheter.

Embodiment 22. The system of Embodiment 21, further comprising a handle coupled to the proximal end of the guide catheter, the handle comprising at least one control operatively connected to the cutting mechanism to enable actuation of the grasping arms between the closed position and the open position and/or to enable actuation of the cutting element.

Embodiment 23. A method of cutting leaflet tissue at a cardiac valve within a body, the method comprising: providing a system for cutting leaflet tissue as in any of the Embodiment 1-22, positioning the guide catheter such that the distal end of the guide catheter is positioned near a targeted cardiac valve; extending the cutting mechanism beyond the distal end of the guide catheter; grasping targeted leaflet tissue between the cutting arm and the one or more grasping arms of the cutting mechanism; and actuating the cutting element of the cutting mechanism to cut the grasped leaflet tissue.

Embodiment 24. The method of Embodiment 23, wherein the one or more grasping arms are positioned on a ventricular side of the targeted leaflet tissue and the cutting arm is positioned on an atrial side of the targeted leaflet tissue when the leaflet tissue is grasped by the cutting mechanism.

Embodiment 25. The method of Embodiment 23 or Embodiment 24, wherein the cutting mechanism is advanced through the leaflet by repeated actuation of the one or more grasping arms between the open and closed positions so as to grasp and cut successive portions of leaflet tissue.

Embodiment 26. The method of any one of Embodiments 23-25, wherein the cutting mechanism is advanced through the leaflet tissue by positioning the one or more grasping arms to a position between a fully closed and fully open position, and moving the cutting mechanism through the leaflet tissue.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. A cutting mechanism configured for cutting leaflet tissue at a cardiac valve, the cutting mechanism comprising:
    a cutting arm having a length extending along a longitudinal axis, the cutting arm including an actuatable cutting element configured to cut targeted leaflet tissue upon sufficient contact with the targeted leaflet tissue;
    a central hinge disposed at or near a distal end of the cutting arm;
    one or more grasping arms each connected to the central hinge and extending therefrom to a respective free end, the one or more grasping arms being rotatable about the central hinge so as to be selectively moveable between
        a closed position wherein the one or more grasping arms are closed substantially against the cutting arm, and
        an open position wherein the one or more grasping arms are opened laterally away from the cutting arm by rotating about the central hinge,
    wherein the cutting mechanism is configured to enable grasping of leaflet tissue between the cutting arm and the one or more grasping arms and to enable the cutting of grasped leaflet tissue via actuation of the cutting element; and
    an auxiliary arm connected to the central hinge and disposed opposite the one or more grasping arms, the auxiliary arm being mechanically connected to the cutting element such that movement of the auxiliary arm as the cutting mechanism moves between the open position and the closed position causes advancement and retraction of the cutting element relative to the cutting arm.

2. The cutting mechanism of claim 1, wherein the cutting mechanism comprises at least a first grasping arm and a second grasping arm in the one or more grasping arms disposed such that, when the cutting mechanism is in the closed position, the first grasping arm is disposed on a first side of the cutting arm and the second grasping arm is disposed on a second, opposite side of the cutting arm.

3. The cutting mechanism of claim 2, wherein the cutting element is disposed on a portion of the cutting arm between the first and second grasping arms so as to enable cutting of leaflet tissue disposed between the first and second grasping arms.

4. The cutting mechanism of claim 2, further comprising a cross bar extending between the first and second grasping arms.

5. The cutting mechanism of claim 4, wherein the cross bar is aligned with the cutting element when the cutting mechanism is in the closed position, or is positioned closer to the central hinge than the cutting element when the cutting mechanism is in the closed position.

6. The cutting mechanism of claim 1, wherein the one or more grasping arms are openable to an angle of up to about 90 degrees from the cutting arm.

7. The cutting mechanism of claim 1, wherein the free ends of the one or more grasping arms curve laterally inward toward the cutting arm.

8. The cutting mechanism of claim 7, wherein the curved free ends of the one or more grasping arms cross over the longitudinal axis of the cutting arm when moving from the open position to the closed position.

9. The cutting mechanism of claim 7, wherein the curved free ends curve laterally inward at an angle of between about 5 degrees and about 20 degrees.

10. The cutting mechanism of claim 1, wherein the cutting element is spring-loaded so as to be capable of actuation from a non-deployed to a deployed state via controlled release of spring energy.

11. The cutting mechanism of claim 1, wherein the central hinge comprises a linkage mechanism configured to convert axial movement of a control rod along the longitudinal axis of the cutting arm into lateral movement of the grasping arms.

12. The cutting mechanism of claim 11, wherein the cutting element is connected to the control rod and extends through a slot of the cutting arm such that actuation of the control rod moves the cutting element within the slot in an axial direction relative to the cutting arm.

13. The cutting mechanism of claim 1, wherein the one or more grasping arms have a length of about 4 mm to about 40 mm.

14. The cutting mechanism of claim 1, wherein the cutting element comprises a sharpened edge.

15. The cutting mechanism of claim 1, wherein the cutting element comprises a tapered needle.

16. The cutting mechanism of claim 1, wherein the cutting element comprises a wire loop configured to provide radio frequency current energy.

17. The cutting mechanism of claim 1, wherein the cutting arm includes a gripping element configured to aid in gripping leaflet tissue in contact with the cutting arm.

18. The cutting mechanism of claim 1, wherein the cutting element comprises at least two or more cutting elements.

19. The cutting mechanism of claim 1, wherein the cutting element has a depth of about 0.4 mm to about 10 mm.

20. A system for cutting leaflet tissue at a cardiac valve, the system comprising:
    a guide catheter having a proximal end and a distal end, wherein the distal end of the guide catheter is steerable to a position above a cardiac valve; and
    a cutting mechanism routable through the guide catheter and configured to extend beyond the distal end of the guide catheter, the cutting mechanism comprising:
        a cutting arm having a length extending along a longitudinal axis, the cutting arm including an actuatable cutting element configured to cut targeted leaflet tissue upon sufficient contact with the targeted leaflet tissue;
        a central hinge disposed at or near a distal end of the cutting arm;
        one or more grasping arms each connected to the central hinge and extending therefrom to a respective free end, the one or more grasping arms being rotatable about the central hinge so as to be selectively moveable between a closed position wherein the one or more grasping arms are closed substantially against the cutting arm, and an open position wherein the one or more grasping arms are opened laterally away from the cutting arm by rotating about the central hinge; and an auxiliary arm connected to the central hinge and disposed opposite the one or more grasping arms, the auxiliary arm being mechanically connected to the cutting element such that movement of the auxiliary arm as the cutting mechanism moves between the open position and the closed position causes advancement and retraction of the cutting element relative to the cutting arm;

wherein the cutting mechanism is configured to enable grasping of leaflet tissue between the cutting arm and the one or more grasping arms and to enable the cutting of grasped leaflet tissue via actuation of the cutting element.

21. The system of claim 20, further comprising a handle coupled to the proximal end of the guide catheter, the handle comprising at least one control operatively connected to the cutting mechanism to enable actuation of the grasping arms between the closed position and the open position and/or to enable actuation of the cutting element.

22. A cutting mechanism configured for cutting leaflet tissue at a cardiac valve, the cutting mechanism comprising:

a cutting arm having a length extending along a longitudinal axis, the cutting arm including an actuatable cutting element configured to cut targeted leaflet tissue upon sufficient contact with the targeted leaflet tissue;

a central hinge disposed at or near a distal end of the cutting arm;

one or more grasping arms each connected to the central hinge and extending therefrom to a respective free end, the one or more grasping arms being rotatable about the central hinge so as to be selectively moveable between a closed position wherein the one or more grasping arms are closed substantially against the cutting arm, and an open position wherein the one or more grasping arms are opened laterally away from the cutting arm by rotating about the central hinge, wherein the cutting mechanism is configured to enable grasping of leaflet tissue between the cutting arm and the one or more grasping arms and to enable the cutting of grasped leaflet tissue via actuation of the cutting element, the central hinge comprises a linkage mechanism configured to convert axial movement of a control rod along the longitudinal axis of the cutting arm into lateral movement of the grasping arms, and the cutting element is connected to the control rod and extends through a slot of the cutting arm such that actuation of the control rod moves the cutting element within the slot in an axial direction relative to the cutting arm.

23. The cutting mechanism of claim 22, wherein the cutting element is spring-loaded so as to be capable of actuation from a non-deployed to a deployed state via controlled release of spring energy.

24. The cutting mechanism of claim 22, wherein the cutting element comprises a sharpened edge.

25. The cutting mechanism of claim 22, wherein the cutting element comprises a tapered needle.

26. The cutting mechanism of claim 22, wherein the cutting element comprises a wire loop configured to provide radio frequency current energy.

* * * * *